United States Patent [19]
Johs et al.

[11] Patent Number: 6,034,777
[45] Date of Patent: Mar. 7, 2000

[54] METHODS FOR UNCORRELATED EVALUATION OF PARAMETERS IN PARAMETERIZED MATHEMATICAL MODEL EQUATIONS FOR WINDOW RETARDENCE, IN ELLIPSOMETER AND POLARIMETER SYSTEMS

[75] Inventors: Blaine D. Johs; Craig M. Herzinger, both of Lincoln, Nebr.

[73] Assignee: J.A. Woollam Co. Inc., Lincoln, Nebr.

[21] Appl. No.: 09/162,217

[22] Filed: Sep. 29, 1998

[51] Int. Cl.$^7$ .................................................... G01N 21/21
[52] U.S. Cl. ............................................. 356/369; 356/365
[58] Field of Search ................................... 356/369, 365, 356/367; 250/225

[56] References Cited

U.S. PATENT DOCUMENTS

| | | | |
|---|---|---|---|
| 5,373,359 | 12/1994 | Woollam et al. | 356/328 |
| 5,504,582 | 4/1996 | Johs et al. | 356/369 |
| 5,521,706 | 5/1996 | Green et al. | 356/369 |
| 5,582,646 | 12/1996 | Woollam et al. | 118/708 |
| 5,666,201 | 9/1997 | Johs et al. | 356/369 |
| 5,706,212 | 1/1998 | Thompson et al. | 364/525 |
| 5,757,494 | 5/1998 | Green et al. | 356/369 |

OTHER PUBLICATIONS

General Treatment of The Effect of Cell Windows in Ellipsometry, Azzam & Bashara, J. of the Optical Society of America, vol. 61, No. 6 (1971).

*Primary Examiner*—Frank G. Font
*Assistant Examiner*—Zandra V. Smith
*Attorney, Agent, or Firm*—James D. Welch

[57] ABSTRACT

Disclosed is a method for evaluating parameters in parameterized equations for independently calculating retardence entered to orthogonal components in a beam of electromagnetic radiation which is caused to pass through spatially separated input and output windows, by each of said input and output windows. The present invention finds application in ellipsometric investigation of sample systems present in vacuum chambers, wherein a beam of electromagnetic radiation is caused to pass through an input window, interact with a sample system, and exit through an output window, and where it is necessary to separate out the effects of said input and output windows to arrive at sample system characterizing results.

31 Claims, 4 Drawing Sheets

6,034,777

METHODS FOR UNCORRELATED EVALUATION OF PARAMETERS IN PARAMETERIZED MATHEMATICAL MODEL EQUATIONS FOR WINDOW RETARDENCE, IN ELLIPSOMETER AND POLARIMETER SYSTEMS

TECHNICAL FIELD

The present invention relates to ellipsometry and polarimetry, and more particularly is a method for evaluating parameters in parameterized equations for use in independently calculating retardence entered to orthogonal components in a beam of electromagnetic radiation which is caused to pass through spatially separated input and output windows.

BACKGROUND

The practice of ellipsometry is well established as a non-destructive approach to determining characteristics of sample systems and can be practiced in real time. The topic is well described in a great many number of publication, one such publication being a review paper by Collins, titled "Automatic Rotating Element Ellipsometers: Calibration, Operation and Real-Time Applications", Rev. Sci. Instrum, 61(8) (1990).

In general, the practice of ellipsometry typically involves causing a spectroscopic beam of electromagnetic radiation, in a known state of polarization, to interact with a sample system at some angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry determines said changes in polarization state by proposing a mathematical model of the ellipsometer system and the sample system investigated by use thereof. Experimental data is then obtained by application of the ellipsometer system, and a square error reducing mathematical regression, (typically), is then applied to the end that parameters in the mathematical model which characterize the sample system are evaluated so that the obtained experimental data, and values calculated by use of the mathematical model are essentially identical.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system;

$PSI=r_p/r_s$; and $DELTA=ARCTAN(<r_p-<r_s>))$.

As alluded to, the practice of ellipsometry requires that a mathematical model be derived and provided for a sample system and for the ellipsometer system being applied. In that light it must be appreciated that an ellipsometer system which is applied ex-situ to investigate a sample system is, generally, sequentially comprised of:

a. a Source of a beam electromagnetic radiation;
b. a Polarizer element;
c. optionally a compensator element;
d. (additional element(s));
e. a sample system;
f. (additional element(s));
g. optionally a compensator element;
h. an Analyzer element; and
i. a Detector System.

Each of said components b.–i. must be accurately represented by a mathematical model of the ellipsometer system along with a vector which represents a beam of electromagnetic radiation provided from said source of a beam electromagnetic radiation.

Various ellipsometer configurations provide that a Polarizer or Analyzer or Compensator(s) can be rotated during data acquisition, and are describe variously as Rotating Polarizer (RAE), Rotating Analyzer (RAE) and Rotating Compensator (RCE) Ellipsometer Systems.

Where an ellipsometer system is applied to investigate a sample system present in a vacuum chamber, it must be appreciated that the beam of electromagnetic radiation must enter through an input window in said vacuum chamber, and exit via an output window therein. In effect this adds said input and output windows as elements in the ellipsometer system as "additional elements", (eg d. and f. above), which additional elements must be accounted for in the mathematical model. If this is not done, sample system representing parameters determined by application of the ellipsometer system will have the effects of said input and output windows at least partially correlated thereinto, much as if the input and output windows were integrally a part of the sample system.

It is further noted that where two sequentially adjacent elements in an ellipsometer system are held in a static position with respect to one another while experimental ellipsometric data is acquired, said two sequentially adjacent elements generally appear to be a single element.

In-situ application of ellipsometry to investigation of a sample system present in a vacuum chamber then presents a challenge to users of ellipsometer systems in the form of providing a mathematical model for each of said input and output windows, and providing a method by which the effects of said windows can be separated from the effects of an investigated sample system. (It is noted that input and output windows in a vacuum chamber are structurally positioned by said vacuum chamber and are not rotatable with respect to a sample system present in said vacuum chamber in use, thus preventing breaking correlation between parameters in equations for sequentially adjacent input and output windows and an investigated sample system by an element rotation technique). While correlation of parameters in mathematical equations which describe the effects of groupings of elements, (such as a compensator and an optional element(s)), can be tolerable, correlation between parameters in the mathematical model of an investigated sample system and other elements in the ellipsometer system must be broken to allow obtaining accurate sample system representing PSI and DELTA values, emphasis added. That is to say that correlation between parameters in a equations in a mathematical model which describe the effects of a stationary compensator and a sequentially next window element, (eg. correlation between effects of elements c. and d. or between f. and g. identified above), in a beam of electromagnetic radiation might be tolerated to the extent that said correlation does not influence determination of sample system describing PSI and DELTA values, but the correlation between parameters in equations which describe the effects of ellipsometer system components (eg. a., b., c., d., f., g., h. and i.), and equations which describe the effects of a present sample system (eg. element e. above), absolutely must be broken to allow the ellipsometer system to provide accurate PSI and DELTA values for said sample system.

Thus is identified an example of a specific problem, solution of which is the topic of the present invention.

One typical approach to overcoming the identified problem, where space consideration are not critical, and where ellipsometer system configuration can be easily modified, is to obtain multiple data sets with an ellipsometer system configured differently during at least two different data set acquisitions. For instance, a data set can be obtained with a sample system present and in which a beam of electromagnetic radiation is caused to interact with said sample system, and another data set can be obtained with the ellipsometer system configured in a straight-through configuration, where a beam of electromagnetic radiation is caused to pass straight through an ellipsometer system without interacting with a sample system. Simultaneous mathematical regression utilizing both data sets can allow evaluation of sample system characterizing PSI and DELTA values over a range of wavelengths, uncorrelated with present bi-refringent retardation effects of said input and output windows. The problem with this approach is that where ellipsometer systems are fit to vacuum chambers, ellipsometer reconfiguration so as to allow acquisition of such multiple data sets can be extremely difficult, if not impossible to carry out.

Another rather obvious solution to the identified problem is to provide input and output windows which are absolutely transparent at all electromagnetic beam wavelengths utilized. That is, provide input and output windows which do not attenuate the magnitude of $r_p$ or $r_s$ orthogonal components, (or at least do not change their ratio, $r_p/r_s$), and which also do not enter phase shift between $r_p$ or $r_s$ orthogonal components when said beam of electromagnetic radiation is caused to pass therethrough. While control of the effect of a window on a ratio, ($r_p/r_s$), of electromagnetic beam orthogonal components can rather successfully, often be accomplished by causing a beam of electromagnetic radiation to approach a surface of a vacuum chamber window along a normal to a surface thereof, this is not the case regarding phase shift entered between $r_p$ and $r_s$ orthogonal components of a said beam of electromagnetic radiation caused to pass therethrough. That is, input and output windows in vacuum chambers typically demonstrate "bi-refringence", in that the $r_p$ orthogonal component is "retarded" by a different amount than is the $r_s$ orthogonal component when said beam of electromagnetic radiation is caused to pass therethrough. To complicate matters, this "bi-refringence" effect also varies with wavelength and with stresses which can develop in a window during use because of temperature and pressure changes etc. This approach is presently utilized with varying degrees of success. For instance, windows provided by BOMCO Inc. —are produced with the goal of eliminating bi-refringence, and are mounted in vacuum chambers using "O" ring seals which help to minimize uneven application of stresses and developed strains thereacross. While some success is achieved via this approach, the BOMCO windows are not "perfect" and do demonstrate some remaining bi-refringence properties, which can an vary in unpredictable ways over a period of usage. In addition, BOMCO windows are expensive, costing on the order of $1000.00 each), and are large in size thereby making adaptation thereof to use in a vacuum chamber difficult at times, particularly in retro-fit scenarios. And, there have been cases where BOMCO windows have broken in use. This is highly undesirable as vacuum chambers are often times caused to contain highly toxic and hazardous materials during, for instance, etching and/or deposition steps required in the fabrication of semiconductor devices.

The alternative to use of the BOMCO windows is to simply use standard vacuum chamber windows, which, while significantly less expensive, demonstrate order of magnitude larger bi-refringence effects. (Note, BOMCO windows provide bi-refringent effects on the order of approximately six-tenths (0.6) to two-tenths (0.2) degrees over a range of wavelengths of from four-hundred (400) to seven-hundred-fifty (750) nanometers, whereas standard vacuum windows demonstrate birefringent effects on the order of six (6.0) to three (3.0) degrees over the same range of wavelengths). (Note, bi-refringent retardation typically follows an approximate inverse wavelength, (eg. 1/wavelength), relationship).

A need is thus identified for a method of practicing ellipsometry which enables the breaking of correlation between parameters in equations which describe retardence entered to orthogonal components of a beam of electromagnetic radiation caused to interact with a sample system, and parameters in equations which describe bi-refringent effects on said orthogonal components in said beam of electromagnetic radiation caused by input and output windows, with a primary, though not limiting, application being in a vacuum chamber setting.

Various researchers have previously noted the identified problem and proposed various first order mathematical model equation correction techniques as solution, which approaches have met with various degrees of success where input and output windows demonstrate on the order of a maximum of two (2) degrees of bi-refringence. This, however, leaves the problem unsolved where bi-refringence approaches six (6.0) degrees, as commonly occurs in standard vacuum windows at wavelengths of four-hundred (400) nanometers and below.

Patents of which the Inventor is aware include U.S. Pat. No. 5,757,494 to Green et al., in which is taught a method for extending the range of Rotating Analyzer/Polarizer ellipsometer systems to allow measurement of DELTAS near zero (0.0) and one-hundred-eighty (180) degrees. Said patent describes the presence of a window-like variable bi-refringent components which is added to a Rotating Analyzer/Polarizer ellipsometer system, and the application thereof during data acquisition, to enable the identified capability.

A patent to Thompson et al. U.S. Pat. No. 5,706,212 teaches a mathematical regression based double fourier series ellipsometer calibration procedure for application, primarily, in calibrating ellipsometers system utilized in infrared wavelength range. Bi-refringent window-like compensators are described as present in the system thereof, and discussion of correlation of retardations entered by sequentially adjacent elements which do not rotate with respect to one another during data acquisition is described therein.

A patent to Woollam et al, U.S. Pat. No. 5,582,646 is disclosed as it describes obtaining ellipsometric data through windows in a vacuum chamber, utilizing other than a Brewster Angle of Incidence.

Patent to Woollam et al, U.S. Pat. No. 5,373,359, patent to Johs et al. U.S. Pat. No. 5,666,210 and patent to Green et al., U.S. Pat. No. 5,521,706, and patent to Johs et al., U.S. Pat. No. 5,504,582 are disclosed for general information as they pertain to Rotating Analyzer ellipsometer systems.

A paper by Johs, titled "Regression Calibration Method for Rotating Element Ellipsometers", Thin Solid Films, 234 (1993) is disclosed as it describes a mathematical regression based approach to calibrating ellipsometer systems.

A paper by Nijs & Silfhout, titled "Systematic and Random Errors in Rotating-Analyzer Ellipsometry", J. Opt. Soc. Am. A., Vol. 5, No. 6, (June 1988), describes a first order mathematical correction factor approach to accounting for window effects in Rotating Analyzer ellipsometers.

A paper by Kleim et al, titled "Systematic Errors in Rotating-Compensator ellipsometry", J. Opt. Soc. Am., Vol 11, No. 9, (September 1994) describes first order corrections for imperfections in windows and compensators in Rotating Compensator ellipsometers.

Principal component analysis and neural network approaches to the problem are discussed in a paper by Pickering et al., titled "Instrumental and Computational Advances for Real-time Processes Control Using Spectroscopic Ellipsometry", Int. Conf. on—Netrology??? and Characterization for VLSI Tech., NIST, (March 1998).

Other papers of interest in the area by Azzam & Bashara include one titled "Unified Analysis of Ellipsometry Errors Due to Imperfect Components Cell-Window Birefringence, and Incorrect Azimuth Angles", J. of the Opt. Soc. Am., Vol 61, No. 5, (May 1971); and one titled "Analysis of Systematic Errors in Rotating-Analyzer Ellipsometers", J. of the Opt. Soc. Am., Vol. 64, No. 11, (November 1974).

Another paper by Straaher et al., titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

Finally, A paper which is co-authored by the inventor herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol.406, (1996) is also disclosed.

In view of relevant prior art, there remains need for a second order mathematical model equation correction technique which enables breaking correlation between sample system characterization DELTA and in-plane retardance entered to a beam of electromagnetic radiation entered by window(s) through which said beam of electromagnetic radiation is caused to pass. This is particularly true where window bi-refringent retardence exceeds a few degrees, as is the case for standard vacuum chamber windows.

DISCLOSURE OF THE INVENTION

The present invention is primarily a method of accurately evaluating parameters in parameterized equations in a mathematical model of a system of spatially separated input and output windows, as applied in an ellipsometry or polarimetery setting. Said parameterized equations enable, when parameters therein are properly evaluated, independent calculation of retardation entered by each of said input window and said output window between orthogonal components of a beam of electromagnetic radiation caused to pass through said input and output windows. (It is to be understood that at least one of said input and output windows is birefringent). In a basic sense, said method comprises, in a functional order, the steps of:

a. providing spatially separated input and output windows, at least one of said input and output windows demonstrating birefringence when a beam of electromagnetic radiation is caused to pass therethrough, there being a means for supporting a sample system positioned between said input and output windows;

b. positioning an ellipsometer system source of electromagnetic radiation and an ellipsometer system detector system such that in use a beam of electromagnetic radiation provided by said source of electromagnetic radiation is caused to pass through said input window, interact with said sample system in a plane of incidence thereto, and exit through said output window and enter said detector system;

c. providing a sample system to said means for supporting a sample system, the composition of said sample system being sufficiently well known so that retardance entered thereby to a polarized beam of electromagnetic radiation of a given wavelength, which is caused to interact with said sample system in a plane of incidence thereto, can be accurately modeled mathematically by a parameterized equation which, when parameters therein are properly evaluated, allows calculation of retardance entered thereby between orthogonal components of a beam of electromagnetic radiation caused to interact therewith in a plane of incidence thereto, given wavelength;

d. providing a mathematical model for said ellipsometer system and said input and output windows and said sample system, comprising separate parameterized equations for independently calculating retardance entered between orthogonal components of a beam of electromagentic radiation caused to pass through each of said input and output windows and interact with said sample system in a plane of incidence thereto; such that where parameters in said mathematical model are properly evaluated, retardance entered between orthogonal components of a beam of electromagentic which passes through each of said input and output windows and interacts with said sample system in a plane of incidence thereto can be independently calculated from said parameterzed equations, given wavelength;

e. obtaining a spectroscopic set of ellipsometric data with said parameterizable sample system present on the means for supporting a sample system, utilizing a beam of electromagnetic radiation provided by said source of electromagnetic radiation, said beam of electromagnetic radiation being caused to pass through said input window, interact with said parameterizable sample system in a plane of incidence thereto, and exit through said output window and enter said detector system;

f. by utilizing said mathematical model provided in step d. and said spectroscopic set of ellipsometric data obtained in step e., simultaneously evaluating parameters in said mathematical model parameterized equations for independently calculating retardance entered between orthogonal components in a beam of electromagnetic radiation caused to pass through said input window, interact with said sample system in a plane of incidence thereto, and exit through said output window.

The end result of practice of said method is that application of said parameterized equations for each of said input window, output window and sample system for which values of parameters therein have been determined in step f., enables independent calculation of retardance entered between orthogonal components of a beam of electromagnetic radiation by each of said input and output windows, and said sample system, at given wavelengths in said spectroscopic set of ellipsometric data. And, it is emphasized that said calculated retardance values for each of said input window, output window and sample system are essentially uncorrelated.

As further discussed supra herein, a modification to the just recited method can be to, (in the step d. provision of a mathematical model for said ellipsometer system and said input and output windows and said parameterizable sample system for each of said input and output windows), provide separate parameterized mathematical model parameterized equations for retardance entered to each of said two orthogonal components of a beam of electromagentic radiation caused to pass through said input and output windows. When this is done, at least one of said orthogonal components for each of said input and output windows is directed out of the plane of incidence of said electromagnetic beam onto said parameterizable sample system. And, typically, though not necessarily, one orthogonal component will be aligned with the plane of incidence of said electromagnetic beam onto said parameterizable sample system. When this is done, calculation of retardation entered between orthogonal components of said beam of electromagnetic radiation, given wavelength, by said input window is provided by comparison of retardance entered to each of said orthogonal components for said input window, and such that calculation of retardation entered between orthogonal components of said beam of electromagnetic radiation, given wavelength, by said output window is provided by comparison of retardance entered to each of said orthogonal components for said output window.

It is pointed out that the step f. simultaneous evaluation of parameters in said mathematical model parameterized equations for said parameterizable sample system, and for said input and output windows, is typically, though not necessarily, achieved by a square error reducing mathematical curve fitting procedure.

It is important to understand that in the method recited infra, the step b. positioning of an ellipsometer system source of electromagnetic radiation and an ellipsometer system detector system includes positioning a polarizer between said source of electromagnetic radiation and said input window, and the positioning of an analyzer between said output window and said detector system, and in which the step e. obtaining of a spectroscopic set of ellipsometric data typically involves obtaining data at a plurality of settings of at least one component selected from the group consisting of: (said analyzer and said polarizer). As well, it is to be understood that additional elements can also be placed between said source of electromagnetic radiation and said input window, and/or between said output window and said detector system, and that the step e. obtaining of a spectroscopic set of ellipsometric data can involve, alternatively or in addition to the recited procedure, obtaining data at a plurality of settings of at least one of said additional components.

It is also to be understood that the step of providing separate parameterized mathematical model parameterized equations for enabling independent calculation of retardance entered by said input and said output windows between orthogonal components of a beam of electromagnetic radiation caused to pass through said input and output windows, and by said sample system, preferably involves parameterized equations having a form selected from the group consisting of:

$ret(\lambda) = (K1/\lambda)$ $ret(\lambda) = (K1/\lambda) * (1 + (K2/\lambda^2))$ $ret(\lambda) = (K1/\lambda) * (1 + (K2/\lambda^2) + (K3/\lambda^4))$ A modified method of accurately evaluating parameters in parameterized equations in a mathematical model of a system of spatially separated input and output windows, said parameterized equations enabling, when parameters therein are properly evaluated, independent calculation of retardation entered by each of said input window and said output window to at least one orthogonal component(s) of a beam of electromagnetic radiation caused to pass through said input and output windows, at least one of said input and output windows being birefringent, said method comprising, in a functional order, the steps of:

a. providing spatially separated input and output windows, at least one of said input and output windows demonstrating birefringence when a beam of electromagnetic radiation is caused to pass therethrough, there being a means for supporting a sample system positioned between said input and output windows;

b. positioning an ellipsometer system source of electromagnetic radiation and an ellipsometer system detector system such that in use a beam of electromagnetic radiation provided by said source of electromagnetic radiation is caused to pass through said input window, interact with said sample system in a plane of incidence thereto, and exit through said output window and enter said detector system;

c. providing a sample system to said means for supporting a sample system;

d. providing a mathematical model for said ellipsometer system and said input and output windows and said sample system, comprising, for each of said input window and said output window, separate parameterized equations for retardance for at least one orthogonal component in a beam of electromagnetic radiation provided by said source of electromagnetic radiation, which orthogonal component is directed out of a plane of incidence which said electromagnetic beam makes with said sample system in use, and optionally providing separate parameterized equations for retardance for an in-plane orthogonal component of said beam of electromagnetic radiation, such that retardation entered to said out-of-plane orthogonal component, and optionally to said in-plane orthogonal component, of said beam of electromagnetic radiation by each of said input and output windows, can, for each of said input and output windows, be separately calculated by said parameterized equations, given wavelength, where parameters in said parameterized equations are properly evaluated;

e. obtaining a spectroscopic set of ellipsometric data with said sample system present on the means for supporting a sample system, utilizing a beam of electromagnetic radiation provided by said source of electromagnetic radiation, said beam of electromagnetic radiation being caused to pass through said input window, interact with said sample system in a plane of incidence thereto, and exit through said output window and enter said detector system;

f. by utilizing said mathematical model provided in step d. and said spectroscopic set of ellipsometric data obtained in step e., simultaneously evaluating sample system DELTA'S in correlation with in-plane orthogonal component retardation entered to said beam of electromagnetic radiation by each of said input and output windows, and parameters in said mathematical model parameterized equations for out-of-plane retardance entered by said input window and said output window to a beam of electromagnetic radiation caused to pass through said input window, interact with said sample system in said plane of incidence thereto, and exit through said output window.

Again, application of said parameterized equations for out-of-plane retardance entered by said input window and said output window to a beam of electromagnetic radiation caused to pass through said input window, interact with said sample system in said plane of incidence thereto, and exit through said output window, for which values of parameters therein are determined in step f., enables independent calculation of retardance entered to said out-of-plane orthogonal component of a beam of electromagnetic radiation by each of said input and output windows, given wavelength.

Also, again the step f. simultaneous evaluation of parameters in said mathematical model parameterized equations for calculation of retardance entered to said out-of-plane orthogonal component of a beam of electromagnetic radiation by each of said input and output windows, given wavelength, and said correlated sample system DELTA'S and retardance entered to said in-plane orthogonal component of a beam of electromagnetic radiation by each of said input and output windows, is typically achieved by a square error reducing mathematical curve fitting procedure.

It remains, in the presently disclosed method, to provide values for parameters in the in-plane parameterized equations for retardance, in said mathematical model of a system of spatially separated input and output windows. The presently disclosed method threfore further comprises the steps of:

g. providing a parameterized equation for retardation entered by said sample system to the in-plane orthogonal component of a beam of electromagnetic radiation, and as necessary similar parameterized equations for retardation entered by each of said input and output windows to the in-plane orthogonal component of a beam of electromagnetic radiation; and h. by utilizing said parameterized mathematical model provided in step d. and said spectroscopic set of ellipsometric data obtained in step e., simultaneously evaluating parameters in said mathematical model parameterized equations for independent calculation of retardance entered in-plane by said sample system and by said input window and said output window such that the correlation between sample system DELTA'S and the retardance entered by said in-plane orthogonal component of a beam of electromagnetic radiation by each of said input and output windows, at given wavelengths in said spectroscopic set of ellipsometric data, is broken.

The end result of practice of the immediately foregoing steps a.–h. is that application of said parameterized equations for each of said input window, output window and sample system for which values of parameters therein have been determined in step h., enables independent calculation of retardance entered to both said out-of-plane and said in-plane orthogonal components of a beam of electromagnetic radiation by each of said input and output windows, and retardance entered by said sample system to said in-plane orthogonal component of said beam of electromagnetic radiation, at given wavelengths in said spectroscopic set of ellipsometric data.

As before for other parameter evaluation steps, the step h. simultaneous evaluation of parameters in said mathematical model parameterized equations for said in-plane retardance entered by said parameterized sample system, and said input and output windows, is typically achieved by a square error reducing mathematical curve fitting procedure.

If the sample system present can not be easily parameterized, the presently disclosed method of accurately evaluating parameters in parameterized equations in a mathematical model of a system of 3spatially separated input and output windows, provides that the following steps, g.–j. be praacticed:

g. removing the sample system from said means for supporting a sample system positioned between said input and output windows, and positioning in its place an alternative sample system for which a parameterized equation for calculating in-plane retardance entered to a beam of electromagnetic radiation, given wavelength, can be provided;

h. providing a parameterized equation for retardation entered in-plane to an orthogonal component of a beam of electromagnetic radiation by said alternative sample system which is then positioned on said means for supporting a sample system positioned between said input and output windows, and as necessary similar parameterized equations for retardation entered by each of said input and output windows to the in-plane orthogonal component of a beam of electromagnetic radiation;

i. obtaining a spectroscopic set of ellipsometric data with said alternative sample system present on the means for supporting a sample system, utilizing a beam of electromagnetic radiation provided by said source of electromagnetic radiation, said beam of electromagnetic radiation being caused to pass through said input window, interact with said alternative sample system in a plane of incidence thereto, and exit through said output window and enter said detector system;

j. by utilizing said parameterized mathematical model for said input window and said output window provided in step d. and said parameterized equation for retardation entered by said alternative sample system provided in step h., and said spectroscopic set of ellipsometric data obtained in step i., simultaneously evaluating parameters in said mathematical model parameterized equations for independent calculation of retardance entered to an in-plane orthogonal component of said beam of electromagnetic radiation by said alternative sample system and by said input window and said output window, such that correlation between DELTA'S entered by said alternative sample system and retardance entered by said in-plane orthogonal component of said beam of electromagnetic radiation, by each of said input and output windows, at given wavelengths in said spectroscopic set of ellipsometric data, is broken, said simultaneous evaluation optionally providing new values for parameters in parameterized equations for calculation of retardance entered in said out-of-plane components of said beam of electromagnetic radiation by each of said input window and said output window;

The end result being that application of said parameterized equations for each of said input window, output window and alternative sample system, for each of which values of parameters therein have been determined in step j., enables independent calculation of retardance entered to both said out-of-plane and said in-plane orthogonal components of a beam of electromagnetic radiation by each of said input window and said output window, and retardance entered by said alternative sample system to said in-plane orthogonal component of a beam of electromagnetic radiation, at given wavelengths in said spectroscopic set of ellipsometric data.

As before, said presently disclosed method of accurately evaluating parameters in parameterized equations in a mathematical model of a system of spatially separated input and output windows provides that in the step j. simultaneous evaluation of parameters in said mathematical model parameterized equations for said in-plane retardation entered by said parameterized sample system, and at least said in-plane input window and output window, is typically achieved by a square error reducing mathematical curve fitting procedure.

As mentioned with respect to the first method of the present invention disclosed herein, the presently disclosed method of accurately evaluating parameters in parameterized equations in a mathematical model of a system of spatially separated input and output windows provides that the step b. positioning of an ellipsometer system source of electromagnetic radiation and an ellipsometer system detector system includes positioning a polarizer between said source of electromagnetic radiation and said input window, and the positioning of an analyzer between said output window and said detector system, and in which the step e. obtaining of a spectroscopic set of ellipsometric data involves obtaining data at a plurality of settings of at least one component selected from the group consisting of: (said analyzer and said polarizer). As well, it is again to be understood that additional elements can also be placed between said source of electromagnetic radiation and said input window, and/or between said output window and said detector system, and that the step e. obtaining of a spectroscopic set of ellipsometric data can involve, alternatively or in addition to the recited procedure, obtaining data at a plurality of settings of at least one of said additional components.

Said presently disclosed method of accurately evaluating parameters in parameterized equations in a mathematical model of a system of spatially separated input and output windows also provides that the step of providing separate parameterized mathematical model parameterized equations for enabling independent calculation of out-of-plane and in-plane retardance entered by said input and said output windows to said beam of electromagnetic radiation caused to pass through said input and output windows, and that retardance entered by a parameterized sample system, involve parameterized equations having a form selected from the group consisting of:

$ret(\lambda)=(K1/\lambda)$ $ret(\lambda)=(K1/\lambda)*(1+(K2/\lambda^2))$ $ret(\lambda)=(K1/\lambda)*(1+(K2/\lambda^2)+(K3/\lambda^4))$ It is again noted that while the present invention can be practiced with any type "windows", be there one or two of them, (ie. one of the input or output windows can be essentially non-birefringent and even ambient), and while an input window or output window can be considered to be a compoiste formed by a plurality of elements, (eg. a compensator and a polarizer), the step a. providing of spatially separated input and output windows is best exemplified as being practiced by the providing of a vacuum chamber that has input and output windows present therein through which an beam of electromagentic radiation is caused to enter and exit, repectively.

Any method of the present invention can further involve, in a functional order the following steps a1.–a4:

a1. fixing evaluated parameter values in mathematical model parameterized equations, for each of said input window and output window, such that said parameterized equations allow independent determination of retardation entered between orthogonal components of a beam of electromagnetic radiation caused to pass through said input and output windows, given wavelength; and a2. causing an unknown sample system to be present on said means for supporting a sample system;

a3. obtaining a spectroscopic set of ellipsometric data with said unknown sample system present on the means for supporting a sample system, utilizing a beam of electromagnetic radiation provided by said source of electromagnetic radiation, said beam of electromagnetic radiation being caused to pass through said input window, interact with said alternative sample system in a plane of incidence thereto, and exit through said output window and enter said detector system; and a4. by utilizing said mathematical model for said input window and said output window in which parameter values in mathematical model parameterized equations, for each of said input window and output window have been fixed, simultaneously evaluating PSI'S and uncorrelated DELTA'S parameters for said unknown sample system.

As in other steps in the present invention method in which parameter values are evaluated, it is again noted that the method of accurately evaluating parameters in parameterized equations in a mathematical model of a system of spatially separated input and output windows in which said simultaneous evaluation of PSI'S and DELTA'S for said unknown sample are typically achieved by a square error reducing mathematical curve fitting procedure.

As alluded to earlier, the step of providing spatially separated input and output windows, at least one of said input and output windows demonstrating birefringent when a beam of electromagnetic radiation is caused to pass therethrough, involves one window which is not birefringent. And, said one window which is not birefringent can be essentially a surrounding ambient, (ie. a phantom window which is essentially just the atmosphere surrounding a sample system).

It is noted that where parameters in parameterized equations for out-of-plane retardacne equations have been determined, a focused version of the present invention method for accurately evaluating parameters in parameterized equations in a mathematical model of a system of spatially separated input and output windows can comprise the steps of b1–b7:

b1. fixing evaluated parameter values in mathematical model parameterized equations, for each of said input window and output window, such that said parameterized equations allow independent determination of retardation entered between orthogonal components of a beam of electromagnetic radiation caused to pass through said input and output windows, given wavelength; and b2. causing an unknown sample system to be present on said means for supporting a sample system;

b3. obtaining a spectroscopic set of ellipsometric data with said unknown sample system present on the means for supporting a sample system, utilizing a beam of electromagnetic radiation provided by said source of electromagnetic radiation, said beam of electromagnetic radiation being caused to pass through said input window, interact with said alternative sample system in a plane of incidence thereto, and exit through said output window and enter said detector system; and b4. by utilizing said mathematical model for said input window and said output window in which parameter values in mathematical model parameterized equations, for each of said input window and output window have been fixed, simultaneously evaluating ALPHA'S and BETA'S for said unknown sample system;

b5. applying transfer functions to said simultaneously evaluated ALPHA'S and BETA'S for said unknown sample system to the end that a data set of effective PSI's and DELTA's for a combination of said windows and said sample system is provided;

b6. providing a mathematical model for said combination of said windows and said sample system which separately accounts for the retardation effects of the presence of said windows and said sample system by parameterized equations; and b7. by utilizing said mathematical model for said combination of said windows and said sample system which separately accounts for the effects of the presence of at least said windows by parameterized equations; and said data set of effective PSI's and DELTA's for a combination of said windows and said sample system, simultaneously evaluating actual PSI's and DELTA's for said unknown sample system per se.

In the case, for instance, where the ellipsometer involved is a Rotating Analyzer, or Rotating Polarizer ellipsometer system, (but not where the ellipsometer involved is a Rotating Compensator System), it is noted that determination of "handedness" is required. Therefore the foregoing method can include, as necessary, providing a mathematical model for said combination of said windows and said sample system which separately accounts for the retardation effects of the presence of said windows and said sample system by parameterized equations which further includes providing for the effects of handedness. It is specifically stated that where the present invention approach of regressing onto effective PSI and DELTA values, (as determined in step b7.), is utilized, the mathematical modle can be derived so that "handedness" is accounted for in arriving at actual PSI's and DELTA's for said unknown sample system per se.

As a generaly comment it is to be understood that separate PSI and DELTA values are achieved for each angle of incidence a beam of electromagnetic radiation makes with respect to a sample substrate and for each wavelength utilized in a spectroscopic range of wavelengths.

The present invention will be better understood by reference to the Detailed Description Section of this Disclosure, with appropriate reference being has to the Drawings.

SUMMARY OF THE INVENTION

It is therefore a primary purpose of the present invention to provide methods for essentially eliminating the effect of windows, such as are present in vacuum chambers, in the analysis of ellipsometric data obtained utilizing an ellipsometer system beam of electromagnetic radiation which passes through said windows.

DETAILED DESCRIPTION

Figure 1A:
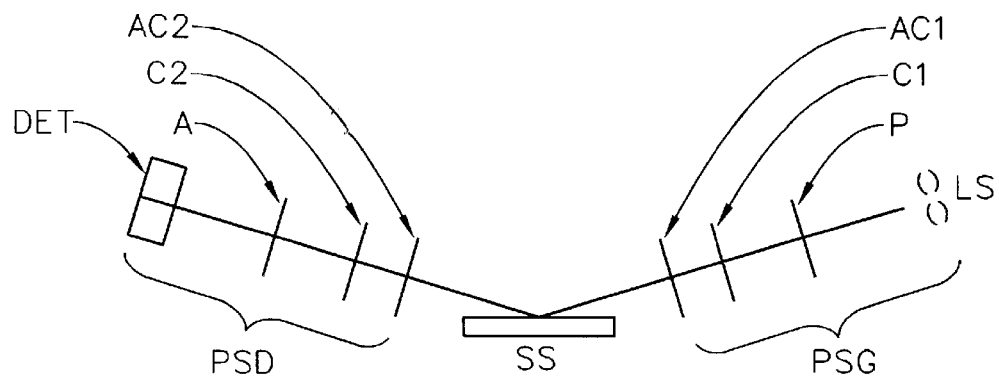
FIG. 1a shows a general elemental configuration of an ellipsometer system.

Turning now to the Drawings, there is shown in FIG. 1a, a general elemental configuration of an ellipsometer system (1) which can be applied to investigate a sample system (SS). Shown are, sequentially:

a. a Source of a beam electromagnetic radiation (LS);
b. a Polarizer element (P);
c. optionally a compensator element (C1);
d. (additional element(s)) (AC1);
e. a sample system (SS);
f. (additional element(s)) (AC2);
g. optionally a compensator element (C2);
h. an Analyzer element (A); and
i. a Detector System (DET).

The elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the present invention Disclosure, vacuum chamber input and output windows.

Figure 1B:
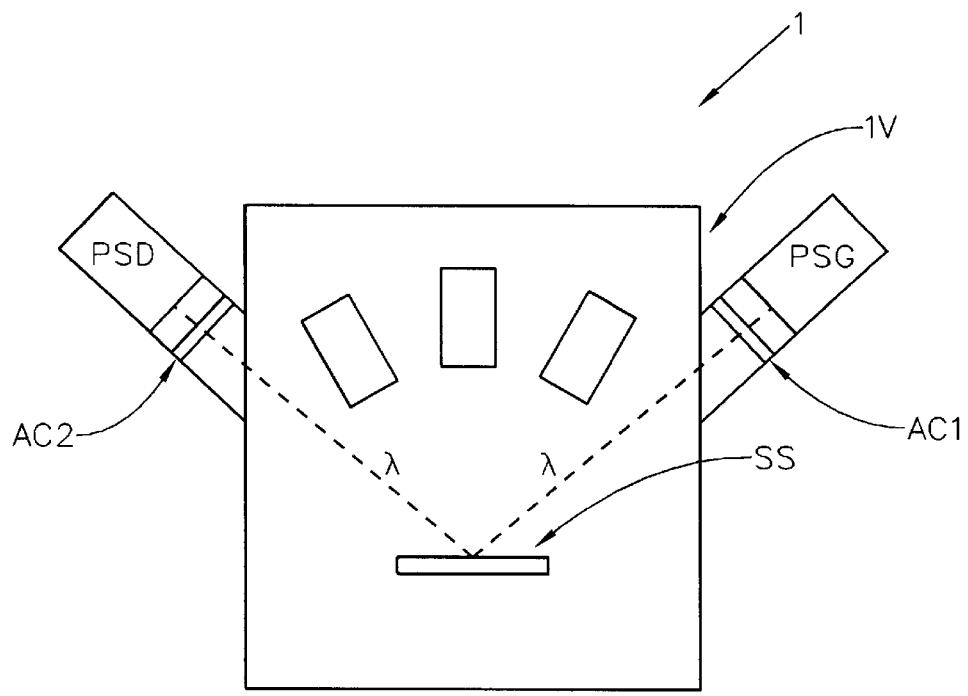
FIG. 1b shows a general diagram of a vacuum chamber, with generally designated Input Window and Output Window present therein.

FIG. 1b shows a general diagram of a vacuum chamber (1v), with generally designated Input Window (AC1) and Output Window (AC2) present therein.

Figure 2A:
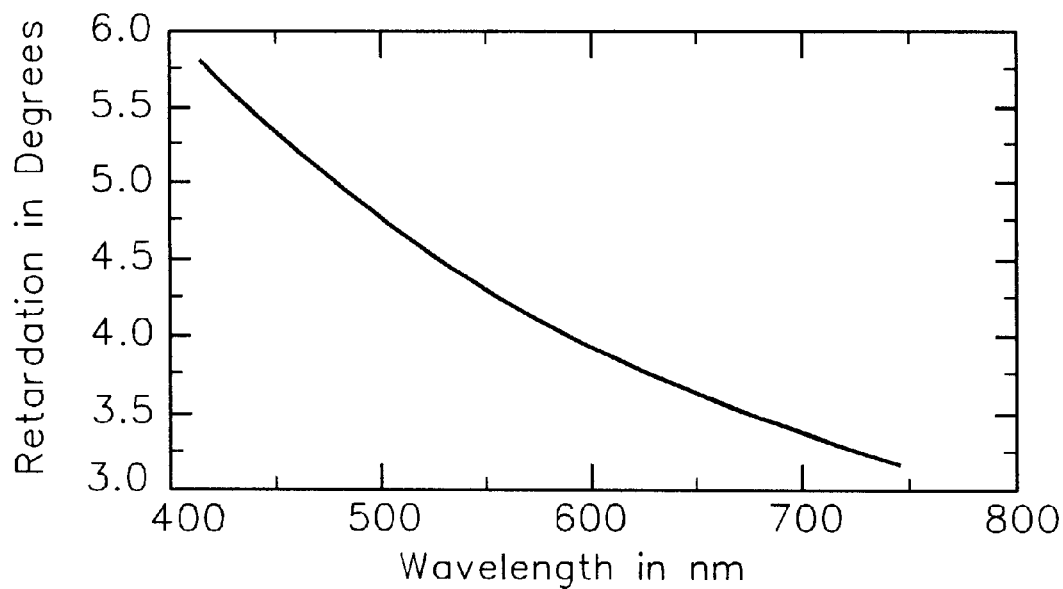
FIG. 2a shows a plot of bi-refringent retardence for a standard vacuum chamber window as a function of wavelength.
Figure 2B:
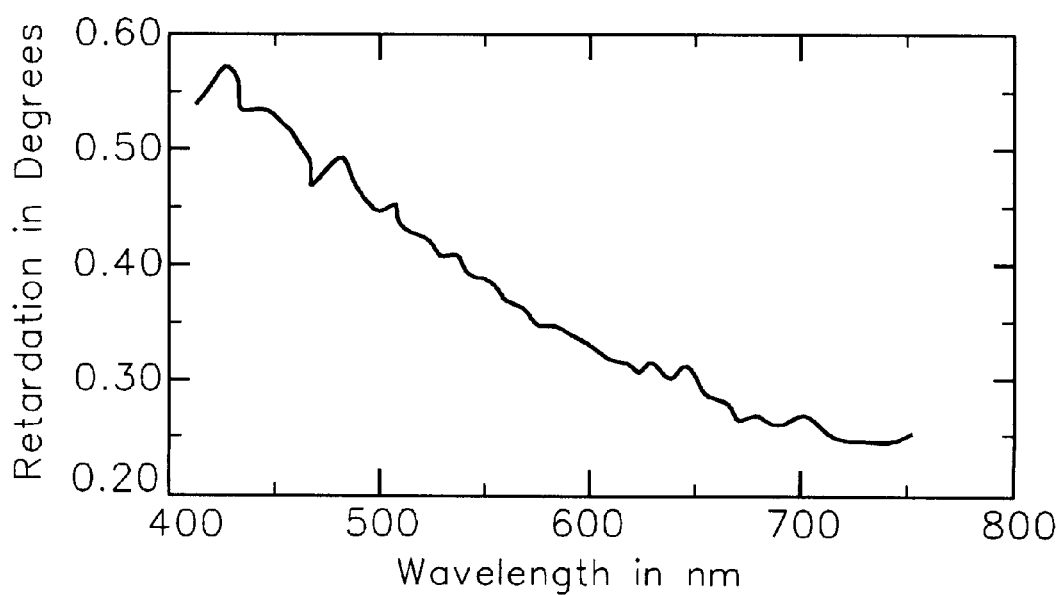
FIG. 2b shows a plot for a BOMCO vacuum chamber window as a function of wavelength.

FIG. 2a, a plot of bi-refringent retardence for a standard vacuum chamber window (AC1) (AC2) as a function of wavelength. For comparison, FIG. 2b shows a similar plot for a BOMCO vacuum chamber window (AC1) (AC2), and it is to be noted that the BOMCO window is significantly less bi-refringent that is the standard vacuum chamber windows. While the BOMCO window characteristics are seen to be greatly superior to those of standard vacuum chamber windows, it is noted that they cost a thousand+ dollars each, and have been known to break during deposition procedures which were being carried out in a vacuum chamber to which they were affixed.

Where, as is generally the case, input (AC1) and output (AC2) windows have bi-refringent characteristics such as shown in FIG. 2a, it must be appreciated that said characteristics must be accounted for in a mathematical model of the ellipsometer and sample system. Where BOMCO windows are utilized, a first order mathematical correction factor approach to accounting for window effects, as described in the Nijs & Silfhout paper cited in the Background Section, titled "Systematic and Random Errors in Rotating-Analyzer Ellipsometry", or as described in the paper by Kleim et al., titled "Systematic Errors in Rotating-Compensator ellipsometry", might be applicable over a some range of wavelengths. However, where standard vacuum chamber windows are utilized, first order corrections have proven to be grossly inadequate.

To provide proof of the validity of the immediately foregoing statement, it Is first necessary to refer to the paper by Johs, titled "Regression Calibration Method for Rotating Element Ellipsometers", which was referenced in the Background Section of this Disclosure. Said paper describes a mathematical regression based approach to calibrating rotating element ellipsometer systems. Said calibration procedure provides that data, (eg. ellipsometric ALPHA and ellipsometric BETA values), be obtained as a function of an ellipsometer system Polarizer Azimuth, as said Polarizer Azimuth is stepped through a range of angles, (eg. sixty (60) degrees to one-hundred-sixty (160) degrees). A mathematical model of the ellipsometer system and a sample system under investigation is provided, and a mathematical square error reducing technique is applied to evaluate parameters in said mathematical model. Successful calibration leads to experimental data and calculated data curves being essentially coincident. The reader is referred to the Johs paper for further insight to the specifics of the calibration technique, which was applied to provide the results shown in FIGS. 3a, 3b, 3c, 4a, 4b, 4c, 5a, 5b, 5c, 6a, 6b and 6c of this Disclosure.

Figure 3A:
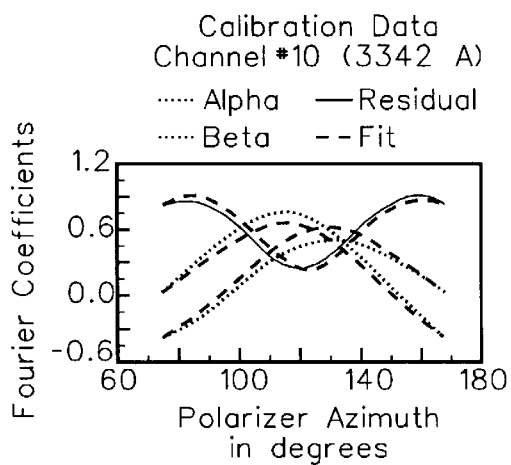
FIGS. 3a, 3b and 3c show ellipsometer system calibration data taken with standard vacuum windows present, at wavelengths of 3342, 5434 and 7277 Angstroms, respectively.
Figure 4A:
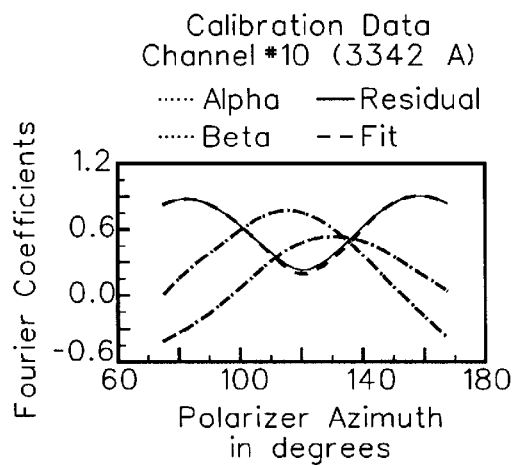
FIGS. 4a, 4b and 4c show similar ellipsometer system calibration data to that in FIGS. 3a, 3b and 3c, taken with standard windows present, and with first order corrections entered to the mathematical model, at wavelengths of 3342, 5434 and 7277 Angstroms, respectively.
Figure 3B:
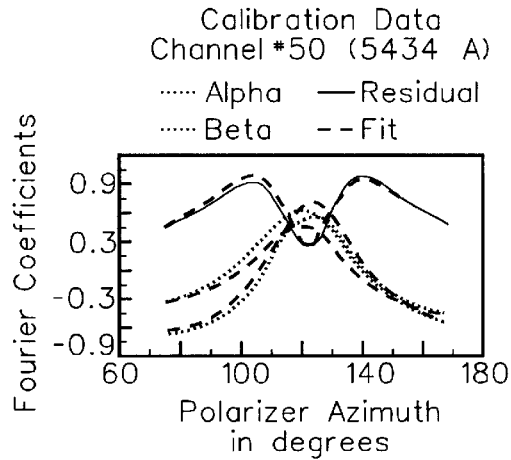
Figure 4B:
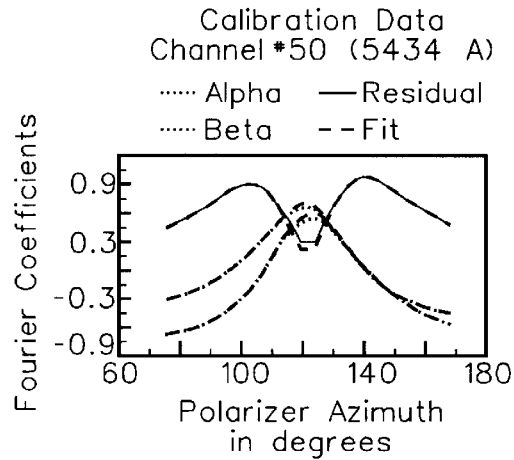
Figure 3C:
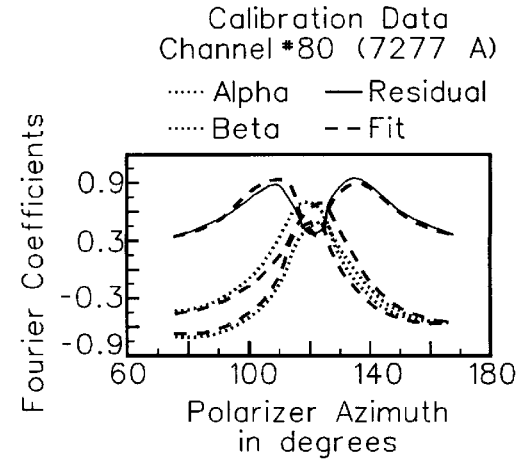
Figure 4C:
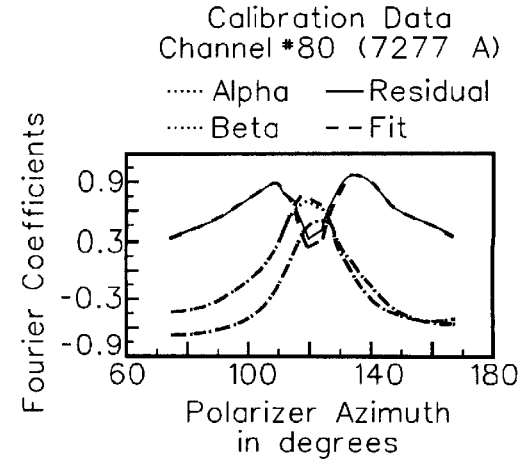
Figure 5A:
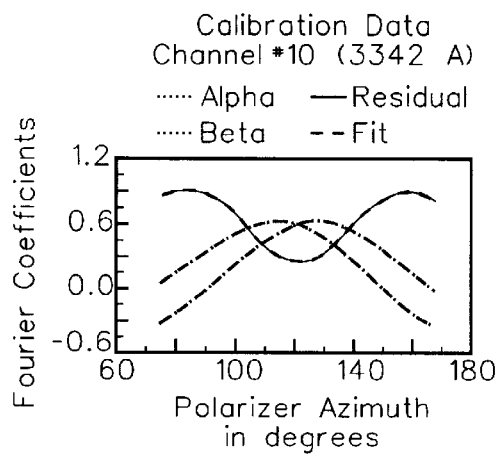
FIGS. 5a, 5b and 5c show ellipsometer system calibration data for the case where no windows are present, at wavelengths of 3342, 5434 and 7277 Angstroms, respectively.
Figure 5B:
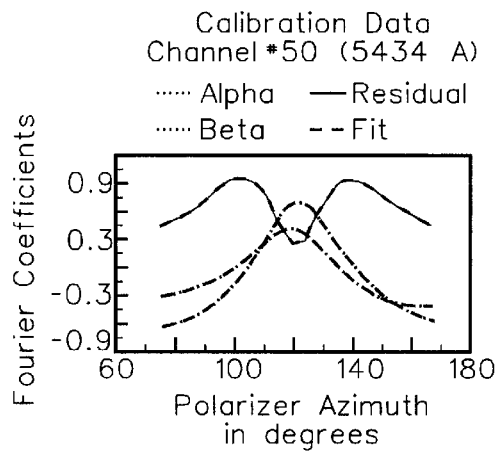
Figure 5C:
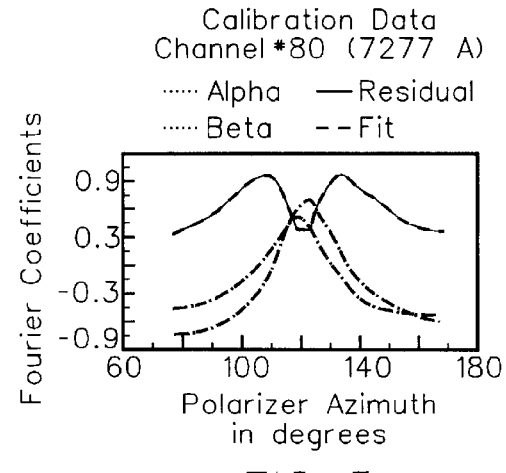

Continuing, FIGS. 3a, 3b and 3c show ellipsometer system calibration data taken with standard windows present, and FIGS. 4a, 4b and 4c show similar ellipsometer system calibration data taken with standard windows present and first order mathematical model corrections applied. FIGS. 3a and 4a are for data taken at a wavelength of 3342 Angstroms, while FIGS. 3b and 4b are for data taken at a wavelength of 5434 Angstroms and FIGS. 3c and 4c are for data taken at a wavelength of 7277 Angstroms. The important thing to note is that the first order corrections, while improving fit between experimental data and mathematical model calculated results for ellipsometric ALPHAS and BETAS, (again see FIGS. 4a, 4b and 4c), do not provide curves as in FIGS. 6a, 6b, and 6c, which correspond to the case where standard windows are present, but where present invention second order corrections are applied. For reference, it is to be noted that FIGS. 5a, 5b and 5c are for the case where no windows are present. For emphasis, it is to be noted that the fit between experimentally obtained ellipsometric ALPHA data and ellipsometric BETA data, and mathematical model calculated ellipsometric ALPHA and ellipsometric BETA data shown in FIGS. 6a, 6b and 6c, (for the case where standard vacuum system windows (AC1) and (AC2) are present and present invention second order corrections are applied in the mathematical model), is as good as is the fit between experimentally obtained ellipsometric ALPHA data and ellipsometric BETA data, and mathematical model calculated ellipsometric ALPHA and ellipsometric BETA data shown in FIGS. 5a, 5b and 5c, (for the case where no windows are present). Thus are demonstrated the benefits and utility of the present invention.

With the benefit of the present invention having then been demonstrated, it remains only to disclose the mathematical basis for, and derivation of, the present invention second order mathematical model corrections, (in the Rotating Analyzer or Polarizer ellipsometer system case), and/or transfer equations, (in the Rotating Compensator ellipsometer system case), which allow directly subtracting away window presence effects. Said derivation requires the use of Matrices which represent the sample, and each element in the ellipsometer system.

To begin it is to be understood that:

1. a beam of electromagnetic radiation from a source thereof can be mathematically modeled as a Stokes Vector:

$$\text{Stokes vector for unpolarized input light: } I = \begin{bmatrix} 1 \\ 0 \\ 0 \\ 0 \end{bmatrix}$$

2. a polarization state insensitive detector can be mathematically modeled as a Stokes Vector:

$$\text{Stokes vector for a polarization insensitive detector 'D': } D = (1\ 0\ 0\ 0)$$

3. a Polarizer P, (or Analyzer A), can be mathematically modeled as Mueller Matrix:

$$\text{Mueller Matrix for a polarizer 'P' or analyzer 'A'}$$

$$P = \begin{bmatrix} 1 & 1 & 0 & 0 \\ 1 & 1 & 0 & 0 \\ 0 & 0 & 0 & 0 \\ 0 & 0 & 0 & 0 \end{bmatrix}$$

4. Azimuthal Rotation as a function of Angle ($\phi$) effected by an element can be modeled by a Mueller Matrix:

$$\text{Azimuthal Rotation Mueller Matrix, as a function of angle } '\phi'.$$

$$R(\phi) = \begin{bmatrix} 1 & 0 & 0 & 0 \\ 0 & \cos(2\phi) & \sin(2\phi) & 0 \\ 0 & -\sin(2\phi) & \cos(2\phi) & 0 \\ 0 & 0 & 0 & 1 \end{bmatrix}$$

5. a Compensator, Retarder or Bi-refringent Window with a Retardance ($\delta$) can be mathematically modeled as:

$$\text{Mueller Matrix for a retarder, compensater 'C', or birefringent window 'W', with a retardance of } '\delta':$$

$$W(\delta) = \begin{bmatrix} 1 & 0 & 0 & 0 \\ 0 & 1 & 0 & 0 \\ 0 & 0 & \cos(\delta) & \sin(\delta) \\ 0 & 0 & -\sin(\delta) & \cos(\delta) \end{bmatrix}$$

6. an isotropic Sample can be mathematically modeled by a Mueller Matrix:

$$\text{Mueller Matrix for a sample 'S':}$$

$$S(\Psi, \Delta) = \begin{bmatrix} 1 & -N & 0 & 0 \\ -N & 1 & 0 & 0 \\ 0 & 0 & C & S \\ 0 & 0 & -S & C \end{bmatrix} \quad \begin{aligned} &\text{where:} \\ &N = \cos(2\Psi) \\ &C = \sin(2\Psi) - \cos(\Delta) \\ &S = \sin(2\Psi) - \sin(\Delta) \end{aligned}$$

A complete Mueller Matrix expression for Signal Intensity out of a Rotating Analyzer ellipsometer system, without windows (AC1) & (AC2) present, can then be written as:

Complete Mueller matrix expression for a rotating analyzer ellipsometer:

Signal_Intensity=$D \cdot (R(-\phi_A) \cdot A \cdot R(\phi_A)) \cdot S \cdot (R(-\phi_P) \cdot P \cdot R(\phi_P)) \cdot I$ or more explicitly as:

$$(1\ 0\ 0\ 0) \cdot \begin{bmatrix} 1 & 0 & 0 & 0 \\ 0 & \cos(2\phi A) & -\sin(2\phi A) & 0 \\ 0 & \sin(2\phi A) & \cos(2\phi A) & 0 \\ 0 & 0 & 0 & 1 \end{bmatrix} \begin{bmatrix} 1 & 1 & 0 & 0 \\ 1 & 1 & 0 & 0 \\ 0 & 0 & 0 & 0 \\ 0 & 0 & 0 & 0 \end{bmatrix} \cdot$$

$$\begin{bmatrix} 1 & 0 & 0 & 0 \\ 0 & \cos(2\phi A) & \sin(2\phi A) & 0 \\ 0 & -\sin(2\phi A) & \cos(2\phi A) & 0 \\ 0 & 0 & 0 & 1 \end{bmatrix} \begin{bmatrix} 1 & -N & 0 & 0 \\ -N & 1 & 0 & 0 \\ 0 & 0 & C & S \\ 0 & 0 & -S & C \end{bmatrix} \cdot$$

$$\begin{bmatrix} 1 & 0 & 0 & 0 \\ 0 & \cos(2\phi P) & -\sin(2\phi P) & 0 \\ 0 & \sin(2\phi P) & \cos(2\phi P) & 0 \\ 0 & 0 & 0 & 1 \end{bmatrix} \begin{bmatrix} 1 & 1 & 0 & 0 \\ 1 & 1 & 0 & 0 \\ 0 & 0 & 0 & 0 \\ 0 & 0 & 0 & 0 \end{bmatrix} \cdot$$

$$\begin{bmatrix} 1 & 0 & 0 & 0 \\ 0 & \cos(2\phi P) & \sin(2\phi P) & 0 \\ 0 & -\sin(2\phi P) & \cos(2\phi P) & 0 \\ 0 & 0 & 0 & 1 \end{bmatrix} \begin{bmatrix} 1 \\ 0 \\ 0 \\ 0 \end{bmatrix}$$

Multiplying this out provides:

Signal_Intensity=$1-\cos(2 \cdot \phi P) \cdot N + (-N+\cos(2 \cdot \phi P)) \cdot \cos(2 \cdot \phi A) + \sin(2 \cdot \phi A) \cdot C \cdot \sin(2 \cdot \phi P)$ and if the Analyzer (A) is rotating as a function of Time, (ie. $\phi A = w \cdot T$), then the above Detector Intensity can be written as "DC" Normalized ellipsometric ALPHA (2w) and BETA (2w) Fourier Coefficients at (2w) frequency:

$$\alpha = \frac{\cos(2 \cdot \phi P) - N}{1 - \cos(2 \cdot \phi P) \cdot N} \qquad \beta = \frac{\sin(2 \cdot \phi P) \cdot C}{1 - \cos(2 \cdot \phi P) \cdot N}$$

Where input and output windows (AC1) and (AC2) are present, and designated as (W1) and (W2) respectively, the Signal Intensity Equation becomes:

Signal_Intensity=$D \cdot (R(-\phi_A) \cdot A \cdot R(\phi_A)) \cdot (R(-\phi_{W2}) \cdot W(\delta 2) \cdot R(\phi_{W2})) \cdot S \cdot (R(-\phi_{W1}) \cdot W(\delta 1) \cdot R(\phi_{W1})) \cdot (R(\phi_P) \cdot P \cdot R(\phi_P)) \cdot I$ Re-evaluating the Rotating Analyzer and the Detector matrices provides:

$$D \cdot (R(-\phi_A) \cdot A \cdot R(\phi_A)) =$$

$$(1\ 0\ 0\ 0) \cdot \begin{bmatrix} 1 & 0 & 0 & 0 \\ 0 & \cos(2\phi A) & -\sin(2\phi A) & 0 \\ 0 & \sin(2\phi A) & \cos(2\phi A) & 0 \\ 0 & 0 & 0 & 1 \end{bmatrix} \begin{bmatrix} 1 & 1 & 0 & 0 \\ 1 & 1 & 0 & 0 \\ 0 & 0 & 0 & 0 \\ 0 & 0 & 0 & 0 \end{bmatrix} \cdot$$

$$\begin{bmatrix} 1 & 0 & 0 & 0 \\ 0 & \cos(2\phi A) & \sin(2\phi A) & 0 \\ 0 & -\sin(2\phi A) & \cos(2\phi A) & 0 \\ 0 & 0 & 0 & 1 \end{bmatrix}$$

Therefore, the ALPHA (2$\phi$A) and BETA (2$\phi$A) of the complete system can be determined by multiplying out the rest of the Mueller Matrices (excluding the Analyzer and Detector Matrices), using:

$$\alpha = \frac{s1}{s0} \qquad \beta = \frac{s2}{s0}$$

Multiplying out the rest of the Mueller Matrices, without any present invention simplifying assumptions provides:

$$\begin{bmatrix} 1 & 0 & 0 & 0 \\ 0 & \cos 2\phi w2 & -\sin 2\phi w2 & 0 \\ 0 & \sin 2\phi w2 & \cos 2\phi w2 & 0 \\ 0 & 0 & 0 & 1 \end{bmatrix} \begin{bmatrix} 1 & 0 & 0 & 0 \\ 0 & 1 & 0 & 0 \\ 0 & 0 & \cos \delta w2 & \sin \delta w2 \\ 0 & 0 & -\sin \delta w2 & \cos \delta w2 \end{bmatrix} \cdot$$

$$\begin{bmatrix} 1 & 0 & 0 & 0 \\ 0 & \cos 2\phi w2 & \sin 2\phi w2 & 0 \\ 0 & -\sin 2\phi w2 & \cos 2\phi w2 & 0 \\ 0 & 0 & 0 & 1 \end{bmatrix} \begin{bmatrix} 1 & -N & 0 & 0 \\ -N & 1 & 0 & 0 \\ 0 & 0 & C & S \\ 0 & 0 & -S & C \end{bmatrix} \cdot$$

$$\begin{bmatrix} 1 & 0 & 0 & 0 \\ 0 & \cos 2\phi w1 & -\sin 2\phi w1 & 0 \\ 0 & \sin 2\phi w1 & \cos 2\phi w1 & 0 \\ 0 & 0 & 0 & 1 \end{bmatrix} \begin{bmatrix} 1 & 0 & 0 & 0 \\ 0 & 1 & 0 & 0 \\ 0 & 0 & \cos \delta w1 & \sin \delta w1 \\ 0 & 0 & -\sin \delta w1 & \cos \delta w1 \end{bmatrix} \cdot$$

$$\begin{bmatrix} 1 & 0 & 0 & 0 \\ 0 & \cos 2\phi w1 & \sin 2\phi w1 & 0 \\ 0 & -\sin 2\phi w1 & \cos 2\phi w1 & 0 \\ 0 & 0 & 0 & 1 \end{bmatrix} \begin{bmatrix} 1 \\ \cos 2\phi P \\ \sin 2\phi P \\ 0 \end{bmatrix} = \begin{bmatrix} s0 \\ s1 \\ s2 \\ s3 \end{bmatrix}$$

$$= \begin{bmatrix} s0 \\ s1 \\ s2 \\ s3 \end{bmatrix}$$

and further:

$s0 = 1 - \cos 2\phi P \cdot N \cdot \cos 2\phi w1^2 - \cos 2\phi P \cdot N \cdot \sin 2\phi w1^2 \cdot \cos \delta w1 \ldots +$ $-\sin 2\phi P \cdot N \cdot \cos 2\phi w1 \cdot \sin 2\phi w1 + \sin 2\phi P \cdot N \cdot \sin 2\phi w1 \cdot \cos \delta w1 \cdot \cos 2\phi w1$ $s1 = -N \cdot \cos 2\phi w2^2 - N \cdot \sin 2\phi w2^2 \cdot \cos \delta w2 + \cos 2\phi P \cdot \cos 2\phi w1^2 \cdot \cos 2\phi w2^2 \ldots +$ $\cos 2\phi P \cdot \cos 2\phi w1^2 \cdot \sin 2\phi w2^2 \cdot \cos \delta w2 \ldots +$ $\cos 2\phi P \cdot \cos 2\phi w1 \cdot \sin 2\phi w1 \cdot C \cdot \cos 2\phi w2 \cdot \sin 2\phi w2 \ldots +$ $-\cos 2\phi P \cdot \cos 2\phi w1 \cdot \sin 2\phi w1 \cdot C \cdot \sin 2\phi w2 \cdot \cos \delta w2 \cdot \cos 2\phi w2 \ldots +$ $\cos 2\phi P \cdot \cos 2\phi w1 \cdot \sin 2\phi w1 \cdot \sin 2\phi w2 \cdot \sin \delta w2 \cdot S \ldots +$ -continued $$\cos 2\phi P \cdot \cos \delta w1 \cdot \sin 2\phi w1^2 \cdot \cos 2\phi w2^2 \ldots +$$
$$\cos 2\phi P \cdot \cos \delta w1 \cdot \sin 2\phi w1^2 \cdot \sin 2\phi w2^2 \cdot \cos \delta w2 \ldots +$$
$$-\cos 2\phi P \cdot \sin 2\phi w1 \cdot \cos \delta w1 \cdot \cos 2\phi w1 \cdot C \cdot \cos 2\phi w2 \cdot \sin 2\phi w2 \ldots +$$
$$\cos 2\phi P \cdot \sin 2\phi w1 \cdot \cos \delta w1 \cdot \cos 2\phi w1 \cdot C \cdot \sin 2\phi w2 \cdot \cos \delta w2 \cdot \cos 2\phi w2 \ldots +$$
$$-\cos 2\phi P \cdot \sin 2\phi w1 \cdot \cos \delta w1 \cdot \cos 2\phi w1 \cdot \sin 2\phi w2 \cdot \sin \delta w2 \cdot S \ldots +$$
$$\cos 2\phi P \cdot \sin 2\phi w1 \cdot \sin \delta w1 \cdot S \cdot \cos 2\phi w2 \cdot \sin 2\phi w2 \ldots +$$
$$-\cos 2\phi P \cdot \sin 2\phi w1 \cdot \sin \delta w1 \cdot S \cdot \sin 2\phi w2 \cdot \cos \delta w2 \cdot \cos 2\phi w2 \ldots +$$
$$-\cos 2\phi P \cdot \sin 2\phi w1 \cdot \sin \delta w1 \cdot \sin 2\phi w2 \cdot \sin \delta w2 \cdot C \ldots +$$
$$\sin 2\phi P \cdot \sin 2\phi w1 \cdot \cos 2\phi w1 \cdot \cos 2\phi w2^2 \ldots +$$
$$\sin 2\phi P \cdot \sin 2\phi w1 \cdot \cos 2\phi w1 \cdot \sin 2\phi w2^2 \cdot \cos \delta w2 \ldots +$$
$$\sin 2\phi P \cdot \sin 2\phi w1^2 \cdot C \cdot \cos 2\phi w2 \cdot \sin 2\phi w2 \ldots +$$
$$-\sin 2\phi P \cdot \sin 2\phi w1^2 \cdot C \cdot \sin 2\phi w2 \cdot \cos \delta w2 \cdot \cos 2\phi w2 \ldots +$$
$$\sin 2\phi P \cdot \sin 2\phi w1^2 \cdot \sin 2\phi w2 \cdot \sin \delta w2 \cdot S \ldots +$$
$$-\sin 2\phi P \cdot \cos 2\phi w1 \cdot \cos \delta w1 \cdot \sin 2\phi w1 \cdot \cos 2\phi w2^2 \ldots +$$
$$-\sin 2\phi P \cdot \cos 2\phi w1 \cdot \cos \delta w1 \cdot \sin 2\phi w1 \cdot \sin 2\phi w2^2 \cdot \cos \delta w2 \ldots +$$
$$\sin 2\phi P \cdot \cos \delta w1 \cdot \cos 2\phi w1^2 \cdot C \cdot \cos 2\phi w2 \cdot \sin 2\phi w2 \ldots +$$
$$-\sin 2\phi P \cdot \cos \delta w1 \cdot \cos 2\phi w1^2 \cdot C \cdot \sin 2\phi w2 \cdot \cos \delta w2 \cdot \cos 2\phi w2 \ldots +$$
$$\sin 2\phi P \cdot \cos \delta w1 \cdot \cos 2\phi w1^2 \cdot \sin 2\phi w2 \cdot \sin \delta w2 \cdot S \ldots +$$
$$-\sin 2\phi P \cdot \cos 2\phi w1 \cdot \sin \delta w1 \cdot S \cdot \cos 2\phi w2 \cdot \sin 2\phi w2 \ldots +$$
$$\sin 2\phi P \cdot \cos 2\phi w1 \cdot \sin \delta w1 \cdot S \cdot \sin 2\phi w2 \cdot \cos \delta w2 \cdot \cos 2\phi w2 \ldots +$$
$$\sin 2\phi P \cdot \cos 2\phi w1 \cdot \sin \delta w1 \cdot \sin 2\phi w2 \cdot \sin \delta w2 \cdot C$$

$$s2 = -\cos 2\phi w2 \cdot \sin 2\phi w2 \cdot N + \cos 2\phi w2 \cdot \sin 2\phi w2 \cdot N \cdot \cos \delta w2 \ldots +$$
$$\cos 2\phi P \cdot \cos 2\phi w1^2 \cdot \cos 2\phi w2 \cdot \sin 2\phi w2 \ldots +$$
$$-\cos 2\phi P \cdot \cos 2\phi w1^2 \cdot \sin 2\phi w2 \cdot \cos \delta w2 \cdot \cos 2\phi w2 \ldots +$$
$$\cos 2\phi P \cdot \cos 2\phi w1 \cdot \sin 2\phi w1 \cdot C \cdot \sin 2\phi w2^2 \ldots +$$
$$\cos 2\phi P \cdot \cos 2\phi w1 \cdot \sin 2\phi w1 \cdot C \cdot \cos 2\phi w2^2 \cdot \cos \delta w2 \ldots +$$
$$-\cos 2\phi P \cdot \cos 2\phi w1 \cdot \sin 2\phi w1 \cdot \cos 2\phi w2 \cdot \sin \delta w2 \cdot S \ldots +$$
$$\cos 2\phi P \cdot \cos \delta w1 \cdot \sin 2\phi w1^2 \cdot \cos 2\phi w2 \cdot \sin 2\phi w2 \ldots +$$
$$-\cos 2\phi P \cdot \cos \delta w1 \cdot \sin 2\phi w1^2 \cdot \sin 2\phi w2 \cdot \cos \delta w2 \cdot \cos 2\phi w2 \ldots +$$
$$-\cos 2\phi P \cdot \sin 2\phi w1 \cdot \cos \delta w1 \cdot \cos 2\phi w1 \cdot C \cdot \sin 2\phi w2^2 \ldots +$$
$$-\cos 2\phi P \cdot \sin 2\phi w1 \cdot \cos \delta w1 \cdot \cos 2\phi w1 \cdot C \cdot \cos 2\phi w2^2 \cdot \cos \delta w2 \ldots +$$
$$\cos 2\phi P \cdot \sin 2\phi w1 \cdot \cos \delta w1 \cdot \cos 2\phi w1 \cdot \cos 2\phi w2 \cdot \sin \delta w2 \cdot S \ldots +$$
$$\cos 2\phi P \cdot \sin 2\phi w1 \cdot \sin \delta w1 \cdot S \cdot \sin 2\phi w2^2 \ldots +$$
$$\cos 2\phi P \cdot \sin 2\phi w1 \cdot \sin \delta w1 \cdot S \cdot \cos 2\phi w2^2 \cdot \cos \delta w2 \ldots +$$
$$\cos 2\phi P \cdot \sin 2\phi w1 \cdot \sin \delta w1 \cdot \cos 2\phi w2 \cdot \sin \delta w2 \cdot C \ldots +$$
$$\sin 2\phi P \cdot \sin 2\phi w1 \cdot \cos 2\phi w1 \cdot \cos 2\phi w2 \cdot \sin 2\phi w2 \ldots +$$
$$-\sin 2\phi P \cdot \sin 2\phi w1 \cdot \cos 2\phi w1 \cdot \sin 2\phi w2 \cdot \cos \delta w2 \cdot \cos 2\phi w2 \ldots +$$
$$\sin 2\phi P \cdot \sin 2\phi w1^2 \cdot C \cdot \sin 2\phi w2^2 \ldots +$$
$$\sin 2\phi P \cdot \sin 2\phi w1^2 \cdot C \cdot \cos 2\phi w2^2 \cdot \cos \delta w2 \ldots +$$
$$-\sin 2\phi P \cdot \sin 2\phi w1^2 \cdot \cos 2\phi w2 \cdot \sin \delta w2 \cdot S \ldots +$$
$$-\sin 2\phi P \cdot \cos 2\phi w1 \cdot \cos \delta w1 \cdot \sin 2\phi w1 \cdot \cos 2\phi w2 \cdot \sin 2\phi w2 \ldots +$$
$$\sin 2\phi P \cdot \cos 2\phi w1 \cdot \cos \delta w1 \cdot \sin 2\phi w1 \cdot \sin 2\phi w2 \cdot \cos \delta w2 \cdot \cos 2\phi w2 \ldots +$$
$$\sin 2\phi P \cdot \cos \delta w1 \cdot \cos 2\phi w1^2 \cdot C \cdot \sin 2\phi w2^2 \ldots +$$

-continued $$\sin2\phi P \cdot \cos\delta w1 \cdot \cos2\phi w1^2 \cdot C \cdot \cos2\phi w2^2 \cdot \cos\delta w2 \ldots +$$

$$-\sin2\phi P \cdot \cos\delta w1 \cdot \cos2\phi w1^2 \cdot \cos2\phi w2 \cdot \sin\delta w2 \cdot S \ldots +$$

$$-\sin2\phi P \cdot \cos2\phi w1 \cdot \sin\delta w1 \cdot S \cdot \sin2\phi w2^2 \ldots +$$

$$-\sin2\phi P \cdot \cos2\phi w1 \cdot \sin\delta w1 \cdot S \cdot \cos2\phi w2^2 \cdot \cos\delta w2 \ldots +$$

$$-\sin2\phi P \cdot \sin\delta w1 \cdot \cos2\phi w1 \cdot \cos2\phi w2 \cdot \sin\delta w2 \cdot C$$

with ellipsometric ALPHA and BETA being given by:

$$\alpha = \frac{s1}{s0}$$

$$\beta = \frac{s2}{s0}$$

Now, the present invention simplification is mathematically based in the fact that input and output rotation matrices involve Sin and Cos of double the rotation angle imposed thereby, and that if an angle of forty-five (45) degrees is assumed for that rotation angle, then the Sin(2θ) becomes 1.0, and the Cos(2θ) becomes 0.0. This assumption is equivalent to saying that each of said input and output window effects two orthogonal components of a beam of electromagnetic radiation passed therethrough differently, and that one of said orthogonal components is oriented "In-The-Plane" of the beam of electromagnetic radiation as it interacts with a sample system, and that the other orthogonal component is oriented "Out-Of-The-Plane" of the beam of electromagnetic radiation as it interacts with a sample system. When this assumption is made, the following hold: for the "In-Plane" orthogonal component:

for in-plane, $\cos2\phi w1 = \cos2w2 = 1$, $\sin2\phi w1 = \sin2\phi w2 = 0$ $$s0 = 1 - \cos2\phi P \cdot N$$

$$s1 = \cos2\phi P - N$$

$$s2 = ((-\cos\delta w1 \cdot \sin\delta w2 - \sin\delta w1 \cdot \cos\delta w2) \cdot S + (\cos\delta w1 \cdot \cos\delta w2 - \sin\delta w1 \cdot \sin\delta w2) \cdot C) \cdot \sin2\phi P$$

$$s2 = \sin2\phi P \cdot (\cos(\delta w1 + \delta w2) \cdot C - \sin(\delta w1 + \delta w2) \cdot S)$$

$$s2 = \sin2\phi P \cdot \sin(2\Psi) \cdot \cos(\Delta + \delta w1 + \delta w2)$$

$$\alpha = \frac{\cos2\phi P - N}{1 - \cos2\phi P \cdot N} \qquad \beta = \frac{\sin2\phi P \cdot \sin(2\Psi) \cdot \cos(\Delta + \delta w1 - \delta w2)}{1 - \cos2\phi P \cdot N}$$

for the "Out-Of-Plane" orthogonal component:

for out-of-plane, $\cos2\phi w1 = \cos2\phi w2 = 0$, $$\sin2\phi w1 = \sin2\phi w2 = 1$$

$$s0 = 1 - \cos2\phi P \cdot N \cdot \cos\delta w1$$

$$s1 = N \cdot \cos\delta w2 - \cos2\phi P \cdot \sin\delta w1 \cdot \sin\delta w2 \cdot C +$$
$$\sin2\phi P \cdot \sin\delta w2 \cdot S + \cos2\phi P \cdot \cos\delta w1 \cdot \cos\delta w2$$

$$s2 = \cos2\phi P \cdot \sin\delta w1 \cdot S - \sin2\phi P \cdot C$$

$$\alpha = \frac{N \cdot \cos\delta w2 - \cos2\phi P \cdot \sin\delta w1 \cdot C + \sin2\phi P \cdot \sin\delta w2 \cdot S + \cos2\phi P \cdot \cos\delta w1 \cdot \cos\delta w2}{1 - \cos2\phi P \cdot N \cdot \cos\delta w1}$$

-continued $$\beta = \frac{\cos2\phi P \cdot \sin\delta w1 \cdot S + \sin2\phi P \cdot C}{1 - \cos2\phi P \cdot N \cdot \cos\delta w1}$$

Figure 6A:
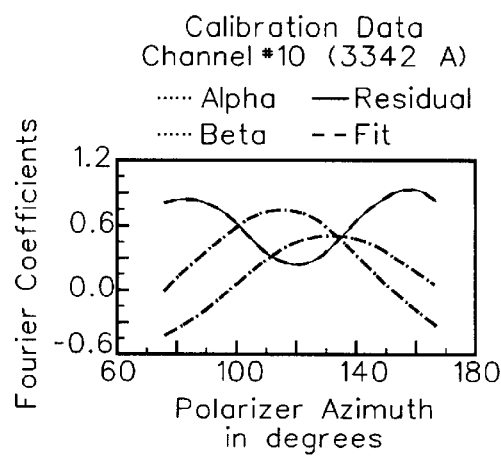
FIGS. 6a, 6b and 6c, show ellipsometer system calibration data for the case where standard vacuum system windows are present and present invention second order corrections are applied in the mathematical model, at wavelengths of 3342, 5434 and 7277 Angstroms, respectively. As good as fit between experimentally obtained ellipsometric ALPHA data and ellipsometric BETA data, and mathematical model calculated ellipsometric ALPHA and ellipsometric BETA data as compared to that shown in FIGS. 5a, 5b and 5c is demonstrated, thereby demonstrating the benefits and utility of the present invention.
Figure 6B:
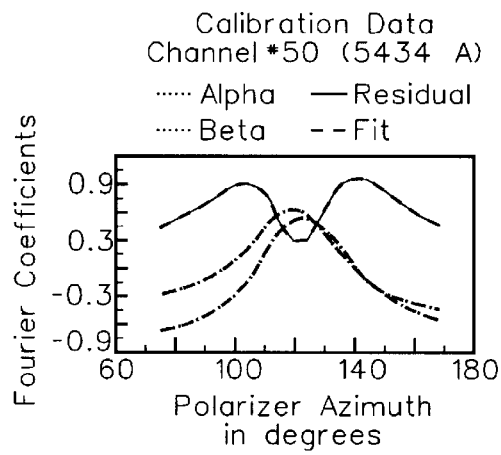
Figure 6C:
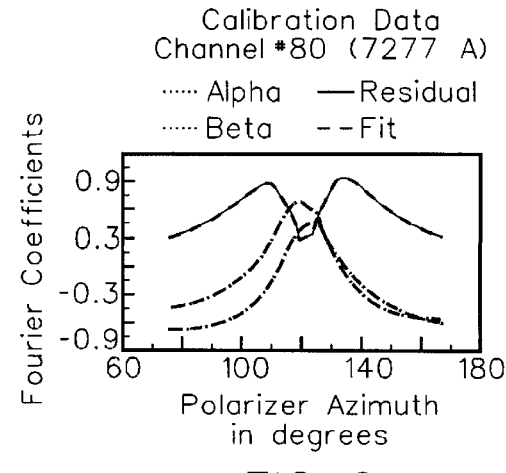

It will be appreciated that the equations for ellipsometric ALPHA and BETA with the present invention simplifying assumption are greatly simplified as compared to the equations for ellipsometric ALPHA and BETA without the present invention simplifying assumption being made. In addition, said simplified equations for ellipsometric ALPHA and BETA provide second order mathematical model correction. And, said present invention second order mathematical model correction equations are of approximately the same level of complexity as are the equations which provide first order mathematical model correction, which, as found in the literature are:

$$\alpha = \frac{\cos2\phi P - N}{1 - \cos2\phi P \cdot N} + \frac{\sin2\phi P \cdot \sin2\phi w2 \cdot \delta w2 \cdot S}{1 - \cos2\phi P \cdot N}$$

$$\beta = \frac{\sin2\phi P \cdot \cos(\Delta + \cos2\phi w2 \cdot \delta w2 + \cos2\phi w1 \cdot \delta w1)}{1 - \cos2\phi P \cdot N} + \frac{\sin2\phi w1 \cdot \delta w1 \cdot \cos2\phi P \cdot S}{1 - \cos2\phi P \cdot N}$$

the application of which are shown by FIGS. 4a, 4b and 4c. Again, for comparison, it is emphasized that FIGS. 6a, 6b and 6c present results of application of the present invention second order mathematical model correction equations.

It is to be further understood that the present invention applies parameterized equations for retardance (Δ) of input and output windows, and for parameterizable sample systems, of the form:

Delta Offset(λ)=DelOff1/λ(1+DelOff2λ$^2$+DelOff3/λ$^4$)

As presented in the Disclosure of the Invention Section of this Disclosure, the present invention includes application of said parameterized equations for input and output window retardance, both in conjunction with, and without, the present invention simplifying assumption that input and output window rotation matrices, which involve the Sin(2θ) and Cos(2θ) of double the rotation angle imposed thereby, have an angle of forty-five (45) degrees assumed for that rotation angle, so that the Sin becomes 1.0, and the Cos becomes 0.0. This assumption, it is to be understood, provides that each orthogonal component of a beam of electromagnetic radiation passing through bi-refringent input and output window is to be treated separately, and that retardence entered between said orthogonal components by passage through an input and/or output window is determined by a comparison of the separate effects on each of said orthogonal components. It is noted that while the present invention mathematical justification for the simplifying assumption is based upon assuming an angle of forty-five (45) degrees for the rotation angle imposed by an input or output window, so that the Sin becomes 1.0, and the Cos becomes 0.0, the concept behind the present invention simplifying assumption is that orthogonal components of a beam of electromagnetic radiation can be considered to each be separately represented by a parameterized retardance equation. When the assumption of angle of forty-five (45) degrees for the rotation angle is made, however, the result is that one orthogonal component is out of the plane of incidence of a beam of electromagnetic radiation which is caused to interact with a sample system, and one orthogonal component thereof is in said plane of incidence. This, of course, means that here a sample can not be provided a parameterized equation for retardence, correlation of retardance entered by the input and output windows "in-plane", and that of a sample system, will exist, and must be broken. Said "in-plane" correlation can be broken by providing a sample system that can be parameterized, and simultaneously evaluating parameters in it, and in parameterized equations for retardance of the input and output windows in a separate calibration procedure.

While the preceding approach works well for analyzing ellipsometric data acquired by a Rotating Analyzer or Rotating Polarizer ellipsometer system wherein windows are present, it is further to be understood that in cases where it is important to extract "true" values for the PSI and DELTA of a sample system, (eg. during in-situ material deposition), additional mathematics is required. The following equations are derived by algebraically inverting the previous equations, and transforming the effective PSI and DELTA measured in the presence of windows into true PSI and DELTA values of a sample system:

$$C2P = \cos 2\phi P; \; S2P = \sin 2\phi P; \; C2A = \cos 2\phi A; \; S2A = \sin 2\phi A$$

$$Nwineff = \cos(2 \cdot \Psi wineff)$$

$$Cwineff = \sin(2 \cdot \Psi wineff) \cdot \cos(\Delta wineff)$$

$$Swineff = \pm \sin(2 \cdot \Psi wineff) \cdot \sin(\Delta wineff)$$

$$s1 = \frac{(C2P - Nwineff)}{1 - Nwineff \cdot C2P} \quad s2 = \frac{Cwineff \cdot S2P}{1 - Nwineff \cdot C2P} \quad s3 = \frac{-Swineff \cdot S2P}{1 - Nwineff \cdot C2P}$$

$$a = (\cos\delta w2 \cdot s1 + \sin\delta w2 \cdot s3) \quad b = s2 \quad c = (\sin\delta w2 \cdot s1 - \cos\delta w2 \cdot s3)$$

$$Ntrue = \frac{(a - \cos\delta w1 \cdot C2P)}{(a \cdot \cos\delta w1 \cdot C2P - 1)}$$

$$Ctrue = \frac{(c \cdot \sin\delta w1 \cdot C2P + S2P \cdot b) \cdot (\cos\delta w1^2 \cdot C2P^2 - 1)}{(\sin\delta w1^2 \cdot C2P^2 + S2P^2) \cdot (a \cdot \cos\delta w1 \cdot C2P - 1)}$$

$$Strue = \frac{(b \cdot \sin\delta w1 \cdot C2P - S2P \cdot c) \cdot (\cos\delta w1^2 \cdot C2P^2 - 1)}{(\sin\delta w1^2 \cdot C2P^2 + S2P^2) \cdot (a \cdot \cos\delta w1 \cdot C2P - 1)}$$

$$\Psi true = a\cos(Ntrue) \cdot 0.5$$

$$\Delta true = a\tan2(Strue, Ctrue) - \text{DeltaOffset}$$

Two roots are calculated by the choosing the sign of the "Swineff" term. Note that when the windows correction terms (δw1) and (δw2) are zero (0.0), the two roots reduce to (+/−Δ), the expected ambiguity for a Rotating Analyzer ellipsometer system.

Continuing, where a Rotating Compensator ellipsometer system is present, use of the same Mueller matrix formalism as for the Rotating Analyzer ellipsometer system, the Fourier coefficients for the Rotating Compensator ellipsometer system can also be derived. The same orthogonalization approach to deriving second order window effects was utilized, (ie. setting the fast axis of window bi-refringence to forty-fve (45) degrees), to determine the out-of-plane window bi-refringence, with the in-plane component being added directly to sample system DELTA. (Note, in the following equations the (δ) is the retardance of the compensator system.

$$DC = \left[\frac{1}{2} \cdot (1 + \cos\delta) \cdot \right.$$

$$\left(\begin{array}{c} -C2P \cdot \cos\delta w1 \cdot N + C2P \cdot \cos\delta w1 \cdot C2A \cdot \cos\delta w2 \ldots + \\ C2P \cdot \sin\delta w1 \cdot S2A \cdot S - C2P \cdot \sin\delta w1 \cdot C2A \cdot \sin\delta w2 \cdot C \ldots + \\ S2P \cdot S2A \cdot C + S2P \cdot C2A \cdot \sin\delta w2 \cdot S \end{array}\right)\right]$$

$$\ldots + 1 - C2A \cdot \cos\delta w2 \cdot N$$

$$\alpha 2 = \left(\begin{array}{c} \sin\delta w1 \cdot N - \sin\delta w1 \cdot C2A \cdot \cos\delta w2 \ldots + \\ \cos\delta w1 \cdot S2A \cdot S - \cos\delta w1 \cdot C2A \cdot \sin\delta w2 \cdot C \end{array}\right) \cdot \sin\delta \cdot S2P$$

$$\beta 2 = \left(\begin{array}{c} -\sin\delta w1 \cdot N + \sin\delta w1 \cdot C2A \cdot \cos\delta w2 \ldots + \\ -\cos\delta w1 \cdot S2A \cdot S + \cos\delta w1 \cdot C2A \cdot \sin\delta w2 \cdot C \end{array}\right) \cdot \sin\delta \cdot C2P$$

$$\alpha 4 = \frac{1}{2} \cdot (1 - \cos\delta) \cdot$$

$$\left(\begin{array}{c} -C2P \cdot \cos\delta w1 \cdot N + C2P \cdot \cos\delta w1 \cdot C2A \cdot \cos\delta w2 \ldots + \\ C2P \cdot \sin\delta w1 \cdot S2A \cdot S - C2P \cdot \sin\delta w1 \cdot C2A \cdot \sin\delta w2 \cdot C \ldots + \\ -S2P \cdot S2A \cdot C - S2P \cdot C2A \cdot \sin\delta w2 \cdot S \end{array}\right)$$

-continued $$\beta 4 = \frac{1}{2} \cdot (1 - \cos\delta) \cdot$$

$$\begin{pmatrix} C2P \cdot S2A \cdot C + C2P \cdot C2A \cdot \sin\delta w2 \cdot S - S2P \cdot \cos\delta w1 \cdot N \ldots + \\ S2P \cdot \cos\delta w1 \cdot C2A \cdot \cos\delta w2 \ldots + \\ S2P \cdot \sin\delta w1 \cdot S2A \cdot S - S2P \cdot \sin\delta w1 \cdot C2A \cdot \sin\delta w2 \cdot C \end{pmatrix}$$

As in the Rotating Analyzer or Rotating Polarizer ellipsometer system case, a global regression calibration can be used to find the Rotating Compensator ellipsometer system calibration parameter values, in addition to out-of-plane window parameterized equation values. And as described infra herein for the Rotating Analyzer ellipsometer system, a standard model fit with a parameterizable sample in place can be carried out to determine values for parameters in-plane.

It is noted that an advantage of the Rotating Compensator ellipsometer system Is that it can correctly measure ellipsometric DELTAS over the full range of zero (0.0) to three-hundred-sixty (360) degrees. This implies that the true PSI and DELTA parameters can be directly inverted at data acquisition time from the measured Fourier Coefficients (Ie. ALPHA and BETA), assuming that parameters in parametric window correction equations for retardance have been previously determined. The inversion equations are:

$$\Psi = \frac{1}{2} \cdot \mathrm{atan}\left[ \frac{\sqrt{\left[\frac{\cos\delta w1 \cdot (1-\cos\delta)\cdot(-S2P\cdot a2 + C2P\cdot b2))\ldots + }{2\cdot\sin\delta\cdot\sin\delta w1\cdot(a4\cdot C2P + b4\cdot S2P)}\right]\ldots +}{4\cdot(-a4\cdot S2P + C2P\cdot b4)^2}}{\left[\frac{(2\cdot\cos\delta w1 \cdot(a4\cdot C2P + b4\cdot S2P))\ldots +}{\frac{(1-\cos\delta)}{\sin\delta}\cdot\sin\delta w1\cdot(S2P\cdot a2 - C2P\cdot b2)}\right]} \right]$$

$$\Delta = \left[\mathrm{atan2}\left[\begin{array}{l}((1-\cos\delta)\cdot\cos\delta w1\cdot(b2\cdot C2P - a2\cdot S2P))\ldots + \\ 2\cdot\sin\delta w1\cdot(a4\cdot C2P + b4\cdot S2P)\end{array}\right.\right.,$$

$$\left.\left. 2\cdot\sin\delta\cdot(b4\cdot C2P - a4\cdot S2P)\right]\right]\ldots + -\mathrm{Delta\_Offset}$$

It is noted that, with a bit of algebra, all the equations for the Rotating Compensator ellipsometer system can be reduced to first order expressions as given in the Kleim et al. reference cited in the Background Section.

In summary, the present invention demonstrates that a methodology for acquiring ellipsometric data through standard vacuum windows has been developed and tested. The key insight enabling said accomplishment is that window bi-refringence can be split into "out-of-plane" and "in-plane" components, where the "plane" referred to is the plane of incidence of an electromagnetic beam of radiation with respect to a sample system. Splitting the electromagnetic beam into said orthogonal components allows derivation of mm second order window corrections which were tractable while allowing an ellipsometer system calibration procedure to determine values of parameters. Again, said ellipsometer system calibration procedure allows parameter values in "out-of-plane" component retardation representing equations to be directly evaluated, with the "in-plane" component being an additive factor to a sample system DELTA. A separate step, utilizing a sample system for which retardation can be modeled by a parameterized equation, allows evaluation of the parameters in parametric equations for the "in-plane" components of windows separately. Work reported in the literature by other researchers provided equations which corrected only first order effects, and said equations have proven insufficient to correct for large, (eg. six (6) degrees), of retardation which is typical in standard vacuum chamber windows. (It is noted that said prior work orthogonal components were derived with respect to window fast axes, which is offset from the sample system plane of incidence). Where the window retardance becomes small, (eg. at longer wavelengths), parameter evaluation in equations for said orthogonal components becomes difficult, as it becomes difficult to determine fast axis orientation. This means that where fast axis orientation can not be identified, algorithm instability becomes a problem. Furthermore, the fast axis orientation of window retardance would also correlate with a sample system DELTA parameter unless a global regression fit using a parameterizable sample system is performed at calibration time.

The present invention methodology comprising two steps disclosed herein, fully and unambiguously determines window correction terms in-situ.

After parameters in parameterized equations for retardance are evaluated by the method of the present invention, ellipsometric data can be taken through windows, (eg. standard vacuum chamber windows), and said data can be quickly and accurately analyzed by applying the window correction factors in a mathematical model for a sample system, (in the case where a Rotating Analyzer ellipsometer system was used to acquire data), or the window effects can be simply quantitatively subtracted away to yield "true" ellipsometric PSI and DELTA values, (in the case where a Rotating Compensator ellipsometer system was used to acquire data).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. A method of accurately evaluating parameters in parameterized equations in a mathematical model of a system of spatially separated input and output windows, said parameterized equations enabling, when parameters therein are properly evaluated, independent calculation of retardation entered by each of said input window and said output window between orthogonal components of a beam of electromagnetic radiation caused to pass through said input and output windows, at least one of said input and output windows being birefringent, said method comprising, in a functional order, the steps of:

a. providing spatially separated input and output windows, at least one of said input and output windows demonstrating birefringence when a beam of electromagnetic radiation is caused to pass therethrough, there being a means for supporting a sample system positioned between said input and output windows;

b. positioning an ellipsometer system source of electromagnetic radiation and an ellipsometer system detector system such that in use a beam of electromagnetic radiation provided by said source of electromagnetic radiation is caused to pass through said input window, interact with a sample system, in a plane of incidence thereto, and exit through said output window and enter said detector system;

c. providing a sample system to said means for supporting a sample system, the composition of said sample system being sufficiently well known so that retardence entered thereby to a polarized beam of electromagnetic radiation of a given wavelength, which is caused to interact with said sample system in a plane of incidence thereto, can be accurately modeled mathematically by a parameterized equation which, when parameters therein are properly evaluated, allows calculation of retardence entered thereby between orthogonal components of a beam of electromagnetic radiation caused to interact therewith in a plane of incidence thereto;

d. providing a mathematical model for said ellipsometer system and said input and output windows and said sample system, comprising separate parameterized equations for independently calculating retardence entered between orthogonal components of a beam of electromagnetic radiation caused to pass through each of said input and output windows and interact with said sample system in a plane of incidence thereto; such that where parameters in said mathematical model are properly evaluated, retardence entered between orthogonal components of a beam of electromagnetic which passes through each of said input and output windows and interacts with said sample system in a plane of incidence thereto can be independently calculated from said parameterized equations;

e. obtaining a spectroscopic set of ellipsometric data with said parameterizable sample system present on the means for supporting a sample system, utilizing a beam of electromagnetic radiation provided by said source of electromagnetic radiation, said beam of electromagnetic radiation being caused to pass through said input window, interact with said parameterizable sample system in a plane of incidence thereto, and exit through said output window and enter said detector system;

f. by utilizing said mathematical model provided in step d. and said spectroscopic set of ellipsometric data obtained in step e., simultaneously evaluating parameters in said mathematical model parameterized equations for independently calculating retardence entered between orthogonal components in a beam of electromagnetic radiation caused to pass through said input window, interact with said sample system in a plane of incidence thereto, and exit through said output window;

to the end that application of said parameterized equations for each of said input window, output window and sample system for which values of parameters therein have been determined in step f., enables independent calculation of retardence entered between orthogonal components of a beam of electromagnetic radiation by each of said input and output windows, and said sample system, at given wavelengths in said spectroscopic set of ellipsometric data, said calculated retardence values for each of said input window, output window and sample system being essentially uncorrelated.

2. A method of accurately evaluating parameters in parameterized equations in a mathematical model of a system of spatially separated input and output windows as in claim 1, in which the step f. simultaneous evaluation of parameters in said mathematical model parameterized equations for said parameterizable sample system, and for said input and output windows, is achieved by a square error reducing mathematical curve fitting procedure.

3. A method of accurately evaluating parameters in parameterized equations in a mathematical model of a system of spatially separated input and output windows as in claim 1, in which the step d. provision of a mathematical model for said ellipsometer system and said input and output windows and said parameterizable sample system, involves, for each of said input and output windows, providing separate parameterized mathematical model parameterized equations for retardence entered to each of said two orthogonal components of a beam of electromagnetic radiation caused to pass through said input and output windows; at least one of said orthogonal components for each of said input and output windows being directed out of the plane of incidence of said electromagnetic beam onto said parameterizable sample system; such that calculation of retardation entered between orthogonal components of said beam of electromagnetic radiation, by said input window is provided by comparison of retardence entered to each of said orthogonal components for said input window, and such that calculation of retardation entered between orthogonal components of said beam of electromagnetic radiation, by said output window is provided by comparison of retardence entered to each of said orthogonal components for said output window.

4. A method of accurately evaluating parameters in parameterized equations in a mathematical model of a system of spatially separated input and output windows as in claim 3, in which the step f. simultaneous evaluation of parameters in said mathematical model parameterized equations for said parameterizable sample system, and for said input and output windows, is achieved by a square error reducing mathematical curve fitting procedure.

5. A method of accurately evaluating parameters in parameterized equations in a mathematical model of a system of spatially separated input and output windows as in claim 1, in which the step b. positioning of an ellipsometer system source of electromagnetic radiation and an ellipsometer system detector system includes positioning a polarizer between said source of electromagnetic radiation and said input window, and the positioning of an analyzer between said output window and said detector system, and in which the step e. obtaining of a spectroscopic set of ellipsometric data involves obtaining data at a plurality of settings of at least one component selected from the group consisting of:

said analyzer; and said polarizer.

6. A method of accurately evaluating parameters in parameterized equations in a mathematical model of a system of spatially separated input and output windows as in claim 3, in which the step b. positioning of an ellipsometer system source of electromagnetic radiation and an ellipsometer system detector system includes positioning a polarizer between said source of electromagnetic radiation and said input window, and the positioning of an analyzer between said output window and said detector system, and in which the step e. obtaining of a spectroscopic set of ellipsometric data involves obtaining data at a plurality of settings of at least one component selected from the group consisting of:

said analyzer; and said polarizer.

7. A method of accurately evaluating parameters in parameterized equations in a mathematical model of a system of spatially separated input and output windows as in claim 1, in which the step of providing separate parameterized mathematical model parameterized equations for enabling independent calculation of retardence entered by said input and said output windows between orthogonal components of a beam of electromagnetic radiation caused to pass through said input and output windows, and by said sample system, involve parameterized equations having a form selected from the group consisting of:

$$ret(\lambda)=(K1/\lambda)$$

$$ret(\lambda)=(K1/\lambda)*(1+(K2/\lambda^2))$$

$$ret(\lambda)=(K1/\lambda)*(1+(K2/\lambda^2)+(K3/\lambda^4)).$$

8. A method of accurately evaluating parameters in parameterized equations in a mathematical model of a system of spatially separated input and output windows as in claim 3, in which the step of providing separate parameterized mathematical model parameterized equations for retardence entered to each of said two orthogonal components of a beam of electromagnetic radiation caused to pass through said input and output window, for each of said input and output windows, thereby enabling independent calculation of retardence entered by said input and entered by said output window between orthogonal components of a beam of electromagnetic radiation caused to pass through said input and output windows, involves, for each input and output window orthogonal retardation component and for said sample system retardation, parameterized equations having a form selected from the group consisting of:

$$ret(\lambda)=(K1/\lambda)$$

$$ret(\lambda)=(K1/\lambda)*(1+(K2/\lambda^2))$$

$$ret(\lambda)=(K1/\lambda)*(1+(K2/\lambda^2)+(K3/\lambda^4)).$$

9. A method of accurately evaluating parameters in parameterized equations in a mathematical model of a system of spatially separated input and output windows as in claim 1, in which the step a. providing of spatially separated input and output windows involves a vacuum chamber.

10. A method of accurately evaluating parameters in parameterized equations in a mathematical model of a system of spatially separated input and output windows as in claim 3, in which the step a. providing of spatially separated input and output windows involves a vacuum chamber.

11. A method of accurately evaluating parameters in parameterized equations in a mathematical model of a system of spatially separated input and output windows as in claims 8 or 6, in which the step b. positioning of an ellipsometer system source of electromagnetic radiation and an ellipsometer system detector system includes positioning additional elements between said source of electromagnetic radiation and said input window, and/or between said output window and said detector system, and in which the step e. obtaining of a spectroscopic set of ellipsometric data involves obtaining data at a plurality of settings of at least one of said additional components.

12. A method of accurately evaluating parameters in parameterized equations in a mathematical model of a system of spatially separated input and output windows, said parameterized equations enabling, when parameters therein are properly evaluated, independent calculation of retardation entered by each of said input window and said output window to at least one orthogonal component(s) of a beam of electromagnetic radiation caused to pass through said input and output windows, at least one of said input and output windows being birefringent, said method comprising, in a functional order, the steps of:

a. providing spatially separated input and output windows, at least one of said input and output windows demonstrating birefringence when a beam of electromagnetic radiation is caused to pass therethrough, there being a means for supporting a sample system positioned between said input and output windows;

b. positioning an ellipsometer system source of electromagnetic radiation and an ellipsometer system detector system such that in use a beam of electromagnetic radiation provided by said source of electromagnetic radiation is caused to pass through said input window, interact with a sample system, in a plane of incidence thereto, and exit through said output window and enter said detector system;

c. providing a sample system to said means for supporting a sample system;

d. providing a mathematical model for said ellipsometer system and said input and output windows and said sample system, comprising, for each of said input window and said output window, separate parameterized equations for retardence for at least one orthogonal component in a beam of electromagnetic radiation provided by said source of electromagnetic radiation, which orthogonal component is directed out-of-a-plane of incidence which said electromagnetic beam makes with said sample system in use, such that retardation entered to said out-of-plane orthogonal component can, for each of said input and output windows, be separately calculated by said parameterized equations, where parameters in said parameterized equations are properly evaluated;

e. obtaining a spectroscopic set of ellipsometric data with said sample system present on the means for supporting a sample system, utilizing a beam of electromagnetic radiation provided by said source of electromagnetic radiation, said beam of electromagnetic radiation being caused to pass through said input window, interact with said sample system in a plane of incidence thereto, and exit through said output window and enter said detector system;

f. by utilizing said mathematical model provided in step d. and said spectroscopic set of ellipsometric data obtained in step e., simultaneously evaluating sample system DELTA'S in correlation with in-plane orthogonal component retardation entered to said beam of electromagnetic radiation by each of said input and output windows, and parameters in said mathematical model parameterized equations for out-of-plane retardence entered by said input window and said output window to a beam of electromagnetic radiation caused to pass through said input window, interact with said sample system in said plane of incidence thereto, and exit through said output window;

to the end that application of said parameterized equations for out-of-plane retardence entered by said input window and said output window to a beam of electromagnetic radiation caused to pass through said input window, interact with said sample system in said plane of incidence thereto, and exit through said output window, for which values of parameters therein are determined in step f., enables independent calculation of retardence entered to said out-of-plane orthogonal component of a beam of electromagnetic radiation by each of said input and output windows.

13. A method of accurately evaluating parameters in parameterized equations in a mathematical model of a system of spatially separated input and output windows as in claim 12, in which the step f. simultaneous evaluation of parameters in said mathematical model parameterized equations for calculation of retardence entered to said out-of-plane orthogonal component of a beam of electromagnetic radiation by each of said input and output windows, and said correlated sample system DELTA'S and retardence entered to said in-plane orthogonal component of a beam of electromagnetic radiation by each of said input and output windows, is achieved by a square error reducing mathematical curve fitting procedure.

14. A method of accurately evaluating parameters in parameterized equations in a mathematical model of a system of spatially separated input and output windows as in claim 11, which further comprises the steps of:

g. providing a parameterized equation for retardation entered by said sample system to the in-plane orthogonal component of a beam of electromagnetic radiation, and as necessary similar parameterized equations for retardance entered by each of said input and output windows to the in-plane orthogonal component of a beam of electromagnetic radiation; and h. by utilizing said parameterized mathematical model provided in step d. and said spectroscopic set of ellipsometric data obtained in step e., simultaneously evaluating parameters in said mathematical model parameterized equations for independent calculation of retardence entered in-plane by said sample system and by said input window and said output window such that the correlation between sample system DELTA'S and the retardence entered by said in-plane orthogonal component of a beam of electromagnetic radiation by each of said input and output windows, at given wavelengths in said spectroscopic set of ellipsometric data, is broken;

to the end that application of said parameterized equations for each of said input window, output window and sample system for which values of parameters therein have been determined in step h., enables independent calculation of retardence entered to both said out-of-plane and said in-plane orthogonal components of a beam of electromagnetic radiation by each of said input and output windows, and retardence entered by said sample system to said in-plane orthogonal component of said beam of electromagnetic radiation, at given wavelengths in said spectroscopic set of ellipsometric data.

15. A method of accurately evaluating parameters in parameterized equations in a mathematical model of a system of spatially separated input and output windows as in claim 14, in which the step h. simultaneous evaluation of parameters in said mathematical model parameterized equations for said in-plane retardance entered by said parameterized sample system, and said input and output windows, is achieved by a square error reducing mathematical curve fitting procedure.

16. A method of accurately evaluating parameters in parameterized equations in a mathematical model of a system of spatially separated input and output windows as in claim 12, which further comprises the steps of:

g. removing the sample system from said means for supporting a sample system positioned between said input and output windows, and positioning in its place an alternative sample system for which a parameterized equation for calculating in-plane retardence entered to a beam of electromagnetic radiation, can be provided;

h. providing a parameterized equation for retardation entered in-plane to an orthogonal component of a beam of electromagnetic radiation by said alternative sample system which is then positioned on said means for supporting a sample system positioned between said input and output windows, and as necessary similar parameterized equations for retardation entered by each of said input and output windows to the in-plane orthogonal component of a beam of electromagnetic radiation;

i. obtaining a spectroscopic set of ellipsometric data with said alternative sample system present on the means for supporting a sample system, utilizing a beam of electromagnetic radiation provided by said source of electromagnetic radiation, said beam of electromagnetic radiation being caused to pass through said input window, interact with said alternative sample system in a plane of incidence thereto, and exit through said output window and enter said detector system;

j. by utilizing said parameterized mathematical model for said input window and said output window provided in step d. and said parameterized equation for retardation entered by said alternative sample system provided in step h., and said spectroscopic set of ellipsometric data obtained in step i., simultaneously evaluating parameters in said mathematical model parameterized equations for independent calculation of retardence entered to an in-plane orthogonal component of said beam of electromagnetic radiation by said alternative sample system and by said input window and said output window, such that correlation between DELTA'S entered by said alternative sample system and retardence entered by said in-plane orthogonal component of said beam of electromagnetic radiation, by each of said input and output windows, at given wavelengths in said spectroscopic set of ellipsometric data, is broken, said simultaneous evaluation optionally providing new values for parameters in parameterized equations for calculation of retardence entered in said out-of-plane components of said beam of electromagnetic radiation by each of said input window and said output window;

to the end that application of said parameterized equations for each of said input window, output window and alternative sample system, for each of which values of parameters therein have been determined in step j., enables independent calculation of retardence entered to both said out-of-plane and said in-plane orthogonal components of a beam of electromagnetic radiation by each of said input window and said output window, and retardence entered by said alternative sample system to said in-plane orthogonal component of a beam of electromagnetic radiation, at given wavelengths in said spectroscopic set of ellipsometric data.

17. A method of accurately evaluating parameters in parameterized equations in a mathematical model of a system of spatially separated input and output windows as in claim 16, in which the step j. simultaneous evaluation of parameters in said mathematical model parameterized equations for said in-plane retardance entered by said parameterized sample system, and at least said in-plane input window and output window, is achieved by a square error reducing mathematical curve fitting procedure.

18. A method of accurately evaluating parameters in parameterized equations in a mathematical model of a system of spatially separated input and output windows as in claim 12, in which the step b. positioning of an ellipsometer system source of electromagnetic radiation and an ellipsometer system detector system includes positioning a polarizer between said source of electromagnetic radiation and said input window, and the positioning of an analyzer between said output window and said detector system, and in which the step e. obtaining of a spectroscopic set of ellipsometric data involves obtaining data at a plurality of settings of at least one component selected from the group consisting of:

said analyzer; and said polarizer.

19. A method of accurately evaluating parameters in parameterized equations in a mathematical model of a system of spatially separated input and output windows as in claim 16, in which the step b. positioning of an ellipsometer system source of electromagnetic radiation and an ellipsometer system detector system includes positioning a polarizer between said source of electromagnetic radiation and said input window, and the positioning of an analyzer between said output window and said detector system, and in which the step i. obtaining of a spectroscopic set of ellipsometric data involves obtaining data at a plurality of settings of at least one component selected from the group consisting of:

said analyzer; and said polarizer.

20. A method of accurately evaluating parameters in parameterized equations in a mathematical model of a system of spatially separated input and output windows as in claim 12, in which the step of providing separate parameterized mathematical model parameterized equations for enabling independent calculation of out-of-plane retardence entered by said input and said output windows to said beam of electromagnetic radiation caused to pass through said input and output windows, involves parameterized equations having a form selected from the group consisting of:

$ret(\lambda) = (K1/\lambda)$ $ret(\lambda) = (K1/\lambda)*(1+(K2/\lambda^2))$ $ret(\lambda) = (K1/\lambda)*(1+(K2/\lambda^2)+(K3/\lambda^4))$.

21. A method of accurately evaluating parameters in parameterized equations in a mathematical model of a system of spatially separated input and output windows as in claim 14, in which the step of providing separate parameterized mathematical model parameterized equations for retardence entered to the out-of-plane and in-plane orthogonal components of a beam of electromagnetic radiation caused to pass through said input and output windows, thereby enabling independent calculation of out-of-plane and in-plane retardence entered by said input and said output window to out-of-plane and in-plane orthogonal components of a beam of electromagnetic radiation caused to pass through said input and output windows, and the step of providing a parameterized equation for in-plane retardence entered by interaction of said bean of electromagnetic radiation with said sample system involve, for each input and output window orthogonal retardation component and for said sample system retardation, parameterized equations having a form selected from the group consisting of:

$ret(\lambda) = (K1/\lambda)$ $ret(\lambda) = (K1/\lambda)*(1+(K2/\lambda^2))$ $ret(\lambda) = (K1/\lambda)*(1+(K2/\lambda^2)+(K3/\lambda^4))$.

22. A method of accurately evaluating parameters in parameterized equations in a mathematical model of a system of spatially separated input and output windows as in claim 16, in which the step of providing separate mathematical model parameterized equations for retardence entered to the out-of-plane and in-plane orthogonal components of a beam of electromagnetic radiation caused to pass through said input and output windows, thereby enabling independent calculation of out-of-plane and in-plane retardence entered by said input and said output window to out-of-plane and in-plane orthogonal components of a beam of electromagnetic radiation caused to pass through said input and output windows, and the step of providing a parameterized equation for in-plane retardence entered by interaction of said bean of electromagnetic radiation with said alternative sample system involve, for each input and output window orthogonal retardation component and for said alternative sample system retardation, parameterized equations having a form selected from the group consisting of:

$ret(\lambda) = (K1/\lambda)$ $ret(\lambda) = (K1/\lambda)*(1+(K2/\lambda^2))$ $ret(\lambda) = (K1/\lambda)*(1+(K2/\lambda^2)+(K3/\lambda^4))$.

23. A method of accurately evaluating parameters in parameterized equations in a mathematical model of a system of spatially separated input and output windows as in claim 12, in which the step a. providing of spatially separated input and output windows involves a vacuum chamber.

24. A method of accurately evaluating parameters in parameterized equations in a mathematical model of a system of spatially separated input and output windows as in claim 16, in which the step a. providing of spatially separated input and output windows involves a vacuum chamber.

25. A method of accurately evaluating parameters in parameterized equations in a mathematical model of a system of spatially separated input and output windows as in claims 1 or 12, which further involves, in a functional order:

fixing evaluated parameter values in mathematical model parameterized equations, for each of said input window and output window, such that said parameterized equations allow independent determination of retardation entered between orthogonal components of a beam of electromagnetic radiation caused to pass through said input and output windows; and causing an unknown sample system to be present on said means for supporting a sample system;

obtaining a spectroscopic set of ellipsometric data with said unknown sample system present on the means for supporting a sample system, utilizing a beam of electromagnetic radiation provided by said source of electromagnetic radiation, said beam of electromagnetic radiation being caused to pass through said input window, interact with said alternative sample system in a plane of incidence thereto, and exit through said output window and enter said detector system; and by utilizing said mathematical model for said input window and said output window in which parameter values in mathematical model parameterized equations, for each of said input window and output window have been fixed, simultaneously evaluating PSI'S and uncorrelated DELTA'S parameters for said unknown sample system.

26. A method of accurately evaluating parameters in parameterized equations in a mathematical model of a system of spatially separated input and output windows as in claims 25, in which said simultaneous evaluation of PSI'S and DELTA'S for said unknown sample are achieved by a square error reducing mathematical curve fitting procedure.

27. A method of accurately evaluating parameters in parameterized equations in a mathematical model of a system of spatially separated input and output windows as in claims 1 or 12, in which the step of providing spatially separated input and output windows, at least one of said input and output windows demonstrating birefringent when a beam of electromagnetic radiation is caused to pass therethrough, involves one window which is not birefringent.

28. A method of accurately evaluating parameters in parameterized equations in a mathematical model of a system of spatially separated input and output windows as in claim 27, in which said at least one window which is not birefringent is essentially a surrounding ambient.

29. A method of accurately evaluating parameters in parameterized equations in a mathematical model of a system of spatially separated input and output windows as in claims 1 or 12 which further involves, in a functional order:

fixing evaluated parameter values in mathematical model parameterized equations, for each of said input window and output window, such that said parameterized equations allow independent determination of retardation entered between orthogonal components of a beam of electromagnetic radiation caused to pass through said input and output windows; and causing an unknown sample system to be present on said means for supporting a sample system;

obtaining a spectroscopic set of ellipsometric data with said unknown sample system present on the means for supporting a sample system, utilizing a beam of electromagnetic radiation provided by said source of electromagnetic radiation, said beam of electromagnetic radiation being caused to pass through said input window, interact with said alternative sample system in a plane of incidence thereto, and exit through said output window and enter said detector system; and by utilizing said mathematical model for said input window and said output window in which parameter values in mathematical model parameterized equations, for each of said input window and output window have been fixed, simultaneously evaluating ALPHA'S and BETA'S for said unknown sample system;

applying transfer functions to said simultaneously evaluated ALPHA'S and BETA'S for said unknown sample system to the end that a data set of effective PSI's and DELTA's for a combination of said windows and said sample system is provided;

providing a mathematical model for said combination of said windows and said sample system which separately accounts for the retardation effects of the presence of said windows and said sample system by parameterized equations; and by utilizing said mathematical model for said combination of said windows and said sample system which separately accounts for the effects of the presence of at least said windows by parameterized equations; and said data set of effective PSI's and DELTA's for a combination of said windows and said sample system, simultaneously evaluating actual PSI's and DELTA's for said unknown sample system per se.

30. A method of accurately evaluating parameters in parameterized equations in a mathematical model of a system of spatially separated input and output windows as in claim 29 in which the step of providing a mathematical model for said combination of said windows and said sample system which separately accounts for the retardation effects of the presence of said windows and said sample system by parameterized equations which further includes providing for the effects of handedness.

31. A method of accurately evaluating parameters in parameterized equations in a mathematical model of a system of spatially separated input and output windows as in claims 29 or 30, in which said evaluation of actual PSI's and DELTA's is achieved by a square error reducing mathematical curve fitting procedure.

* * * * *